(12) United States Patent
Liang et al.

(10) Patent No.: US 6,777,417 B2
(45) Date of Patent: Aug. 17, 2004

(54) 3-(4,5,6,7-TETRAHYDROINDOL-2-YLMETHYLIDIENE-2-INDOLINONE DERIVATIVES AS KINASE INHIBITORS

(75) Inventors: Congxin Liang, Sunnyvale, CA (US); Huiping Guan, South San Francisco, CA (US); Peng Cho Tang, Moraga, CA (US); Robert A. Blake, San Carlos, CA (US)

(73) Assignee: Sugen, Inc., South San Francisco, CA (US)

( * ) Notice: Subject to any disclaimer, the term of this patent is extended or adjusted under 35 U.S.C. 154(b) by 20 days.

(21) Appl. No.: 10/238,051

(22) Filed: Sep. 10, 2002

(65) Prior Publication Data

US 2003/0119819 A1 Jun. 26, 2003

Related U.S. Application Data

(60) Provisional application No. 60/318,508, filed on Sep. 10, 2001.

(51) Int. Cl.⁷ .................. A61K 31/495; C07D 403/06
(52) U.S. Cl. ............................. 514/254.09; 544/373
(58) Field of Search ............... 514/254.09; 544/337, 544/373

(56) References Cited

U.S. PATENT DOCUMENTS

| | | | |
|---|---|---|---|
| 5,466,823 A | 11/1995 | Talley et al. | |
| 5,633,272 A | 5/1997 | Talley et al. | |
| 5,932,598 A | 8/1999 | Talley et al. | |
| 5,968,974 A | 10/1999 | Kargman et al. | |
| 6,114,371 A | * 9/2000 | Tang et al. | 514/414 |
| 6,130,238 A | 10/2000 | Tang et al. | |
| 6,147,106 A | 11/2000 | Tang et al. | |

FOREIGN PATENT DOCUMENTS

| | | |
|---|---|---|
| WO | WO 98/50356 A1 | 11/1998 |
| WO | WO 99/11605 A1 | 3/1999 |
| WO | WO 00/08202 A3 | 2/2000 |
| WO | WO 01/60814 A2 | 8/2001 |

OTHER PUBLICATIONS

Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," *J. Med. Chem.*, 2000, pp. 2655–2663, vol. 43, No. 14, ©American Chemical Society.

International Search Report dated Jan. 3, 2003, from corresponding application, PCT/US02/25974.

E. Fingl et al., "Section I Introduction, Chapter 1—General Principles," *The Pharmacological Basis of Therapeutics*, Fifth Edition, 1975, pp 1–41, Macmillan Publishing Co., Inc., New York, NY.

* cited by examiner

*Primary Examiner*—Ceila Chang
*Assistant Examiner*—Ebenezer Sackey
(74) *Attorney, Agent, or Firm*—Beth A. Burrous; Foley & Lardner LLP

(57) ABSTRACT

The present invention relates to certain 3-(4,5,6,7-tetrahydroindol-2-yl-methylidene)-2-indolinone derivatives that inhibit kinases, in particular Src kinase. Pharmaceutical compositions comprising these compounds, methods of treating diseases mediated by kinases utilizing pharmaceutical compositions comprising these compounds, and methods of preparing them are also disclosed.

4 Claims, No Drawings

3-(4,5,6,7-TETRAHYDROINDOL-2-YLMETHYLIDIENE-2-INDOLINONE DERIVATIVES AS KINASE INHIBITORS

CROSS-REFERENCE TO RELATED APPLICATIONS

This application claims priority under 35 U.S.C. 119(e) to U.S. Provisional Application Serial No. 60/318,508, filed Sep. 10, 2001, the disclosure of which is incorporated by reference herein in its entirety.

BACKGROUND OF THE INVENTION

1. Field of Invention

The present invention relates to certain 3-(4,5,6,7-tetrahydroinol-2-ylmethylidene) -2-indolinone derivatives that inhibit kinases, in particular Src kinase. Pharmaceutical compositions comprising these compounds, methods of treating diseases mediated by kinases, in particular Src kinase, utilizing pharmaceutical compositions comprising these compounds, and methods of preparing them are also disclosed.

2. State of the Art

Src is a cytoplasmic tyrosine kinase implicated in tumor growth, angiogenesis, survival, and invasion ((see., Irby and Yeatman. Role of Src expression and activation in human cancer. Oncogene 19: 5636–5642 (2000)). An activated form, v-Src, is a viral oncogene in chickens. Rare point mutations have been identified in advanced colon tumors and endometrial cancer. Src and/or its close relative Yes have been found to be overexpressed and/or activated in breast, colon, pancreatic, head and neck squamous cell carcinoma, hepatocellular carcinoma, and bladder tumors. Src and Yes are more highly activated/expressed in metastases than in primary colon tumors. Src activity is an independent negative predictor for survival in colon cancer. In mice, inhibition of Src via antisense RNA suppresses growth of human colon and ovarian tumor xenografts. Src is also implicated in certain types of bone disorders. For example, genetic ablation of Src in mice results in osteoporosis ((see., Tanaka et al., 1996 and Susa et al. Src inhibitors: Drugs for the treatment of osteoporosis, cancer or both? Trends Pharm. Sci. 489–495 (2000)) and Src has been shown to be critical for osteoclast-mediated bone resorption. Therefore Src is an attractive target for treating certain types of cancers and bone diseases such as osteoporosis.

SUMMARY OF THE INVENTION

In one aspect, the present invention relates a compound of Formula (I):

(I)

wherein:
Y is methylene, ethylene, carbonyl, or —COCH$_2$—;
m is 0 or 1;

$R^1$ is —S(O)$_n$R$^5$ (where n is 0, 1, or 2 and R$^5$ is alkyl or aralkyl) or —SO$_2$NR$^6$R$^7$ where R$^6$ and R$^7$ are independently hydrogen, alkyl, cycloalkyl, alkoxyalkyl, or hydroxyalkyl;
$R^2$ is hydrogen, alkyl, or hydroxyalkyl;
$R^3$ is alkyl or hydroxyalkyl; or
$R^2$ and $R^3$ together with the nitrogen atom to which they are attached form a heterocycloamino group;
$R^4$ is:
 (a) hydrogen;
 (b) —PO(OR$^8$)$_2$ where each R$^8$ is independently hydrogen or alkyl;
 (c) —COR$^9$ where R$^9$ is alkyl; or
 (d) —CHR$^{10}$NR$^{11}$R$^{12}$ where R$^{10}$ is hydrogen or alkyl, and R$^{11}$ and R$^{12}$ are independently hydrogen or alkyl or R$^{11}$ and R$^{12}$ together with the nitrogen atom to which they are attached form heterocycloamino; or a pharmaceutically acceptable salt thereof.

In a second aspect this invention is directed to a pharmaceutical composition comprising one or more compound(s) of Formula (I) or a pharmaceutically acceptable salt thereof and a pharmaceutically acceptable excipient.

In a third aspect, this invention is directed to a method of treating diseases mediated by abnormal Src kinases (such as Src, Yes, Fyn, Lyn, Lck, in particular Src), activity in an organism, in particular humans, which method comprises administering to said organism a pharmaceutical composition comprising a compound of Formula (I) or a pharmaceutically acceptable salt thereof and a pharmaceutically acceptable excipient. Such diseases include by way of example and not limitation, cancers and bone diseases such as osteoporosis. The compounds of this invention can also regulate the activity of other kinases (PKs) such as EGF, Met, HER2, HER3, HER4, IR, IGF-1R, IRR, PDGFRα, PDGFRβ, CSFIR, C-Kit, C-fms, Flk-1R, Flk4, KDR/Flk-1, Flt-1, Flt3, FGFR-1R, FGFR-2R, FGFR-3R, FGFR-4R, Frk, Btk, Csk, Abl, ZAP70, Fes/Fps, Fak, Jak, Ack, Blk, Hck, Fgr, Yrk, CDK2 and Raf. Accordingly, the compounds of this invention are also useful in treating diseases in humans which are mediated by these kinases.

In a fourth aspect, this invention is directed to a method of modulating the catalytic activity (e.g., inhibiting the catalytic activity) of Src family of kinases such as Src, Yes, Fyn, Lyn, Lck, in particular Src, using a compound of this invention or a pharmaceutical composition comprising a compound of this invention and a pharmaceutically acceptable excipient. The method may be carried out in vitro or in vivo. The compounds of this invention can also modulat the catalytic acitivities of other PKs, in particular receptor tyrosine kinases (RTKs), non-receptor protein tyrosine kinases (CTKs) and serine/threonine protein kinases (STKs) in vitro and/or in vivo. In particular, the other tyrosine kinases whose catalytic activity is modulated by a compound of this invention is selected from the group consisting of Met, EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, Flt3, FGFR-1R, FGFR-2R, FGFR-3R and FGFR-4R. The cellular tyrosine kinase whose catalytic activity is modulated by a compound of this invention is selected from the group consisting of Frk, Btk, Csk, Abl, ZAP70, Fes/Fps, Fak, Jak, Ack, Blk, Hck, Fgr and Yrk. The serine-threonine protein kinase whose catalytic activity is modulated by a compound of this invention is selected from the group consisting of CDK2 and Raf.

In a fifth aspect, this invention is directed to the use of a compound of Formula (I) in the preparation of a medicament useful in the treatment of a disease mediated by abnormal activity of Src family of kinases, in particular Src kinase.

In a sixth aspect, this invention is directed to a method of preparing a compound of Formula (I) which method comprises reacting a compound of formula 1:

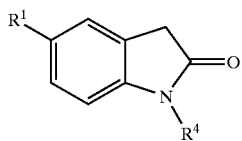

where $R^1$ is as defined in the Summary of the Invention, with a 4,5,6,7-tetrahydro-1H-indole-2-carbaldehyde of formula 2:

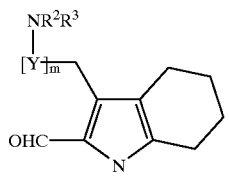

where Y, m, and $R^2$ and $R^3$ are as defined in the Summary of the invention, in the presence of a base;
(i) optionally modifying any of the $R^1$–$R^4$ groups; and
(ii) optionally preparing an acid addition salt; and
(iii) optionally preparing a free base.

Lastly, this invention is also directed to a method of identifying a chemical compound that modulates the catalytic activity of a protein kinase utilizing a compound of Formula (I) as a reference which method comprises by contacting cells expressing said protein kinase with said compound or a compound of Formula (I) or its pharmaceutically acceptable salt and then monitoring said cells for an effect.

DETAILED DESCRIPTION OF THE INVENTION

Definitions

Unless otherwise stated the following terms used in the specification and claims have the meanings discussed below:

"Alkyl" refers to a saturated straight or branched hydrocarbon radical of one to six carbon atoms, preferably one to four carbon atoms e.g., methyl, ethyl, propyl, 2-propyl, n-butyl, iso-butyl, tert-butyl, pentyl, hexyl, and the like, preferably methyl, ethyl, propyl, or 2-propyl.

"Alkylene" refers to a saturated straight or branched hydrocarbon divalent radical of one to six carbon atoms, preferably one to four carbon atoms e.g., methylene, ethylene, propylene, 2-propylene, n-butylene, iso-butylene, tert-butylene, pentylene, hexylene, and the like, preferably methylene, ethylene, propylene, or 2-propylene.

"Cycloalkyl" refers to a 3 to 8 member carbocyclic ring. Examples, without limitation, of cycloalkyl groups are cyclopropane, cyclobutane, cyclopentane, cyclopentene, cyclohexane, and the like.

"Alkoxy" means a radical —OR where R is an alkyl as defined above e.g., methoxy, ethoxy, propoxy, butoxy and the like.

"Alkylthio" means a radical —SR where R is an alkyl as defined above e.g., methylthio, ethylthio, propylthio, and the like.

"Alkoxycarbonyl" means a radical —COOR where R is an alkyl as defined above e.g., methoxycarbonyl, ethoxycarbonyl, propoxycarbonyl, butoxycarbonyl, and the like.

"Alkoxycarbonylalkyl" means a radical -(alkylene)-COOR where R is an alkylene group as defined above e.g., methoxycarbonylmethylene, ethoxycarbonylmethylene, propoxycarbonylmethylene, butoxycarbonylmethylene, methoxycarbonylethylene, ethoxycarbonylethylene, propoxycarbonylethylene, butoxycarbonylethylene, and the like.

"Alkylamino" and "dialkylamino" means a radical —NHR and —NRR' respectively, where R and R' independently represent an alkyl group as defined herein. Representative examples include, but are not limited to methylamino, ethylamino, propylamino, dimethylamino, methylethylamino, di(1-methylethyl)amino, and the like.

"Halo" means fluoro, chloro, bromo, or iodo, preferably fluoro and chloro.

"Haloalkyl" means alkyl substituted with one or more, preferably one, two or three, same or different halo atoms, e.g., —$CH_2Cl$, —$CF_3$, —$CH_2CF_3$, —$CH_2CCl_3$, and the like.

"Haloalkoxy" means a radical —OR where R is an haloalkyl as defined above e.g., trifluoromethoxy, trichloroethoxy, 2,2-dichloropropoxy, and the like.

"Hydroxyalkyl" means a saturated straight or branched monovalent hydrocarbon radical of one to six carbon atoms substituted with one or two hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl,2,3-dihydroxypropyl, and 1-(hydroxymethyl)-2-hydroxyethyl.

"Hydroxyalkylcarbonyl" means —COR where R is hydroxyalkyl as defined above. Representative examples include, but are not limited to, 2-hydroxyethylcarbonyl, 2-hydroxypropylcarbonyl, 3-hydroxypropylcarbonyl, 1-(hydroxymethyl)-2-methylpropylcarbonyl, 2-hydroxybutylcarbonyl, 3-hydroxybutylcarbonyl, 4-hydroxybutylcarbonyl, 2,3-dihydroxypropylcarbonyl, 2,3-dihydroxybutylcarbonyl, and the like.

"Alkoxyalkyl" means a saturated straight or branched monovalent hydrocarbon radical of one to six carbon atoms substituted with one or two alkoxy groups as defined above, e.g., methoxymethyl, 2-methoxyethyl, 2-methoxypropyl, 3-methoxypropyl, ethoxymethyl, 2-ethoxyethyl, and the like.

"Acyl" means a radical —C(O)R where R is hydrogen, alkyl, haloalkyl or cycloalkyl as defined herein, e.g., formyl, acetyl, trifluoroacetyl, butanoyl, cyclopropylcarbonyl, and the like.

"Carboxyalkyl" means a saturated straight or branched monovalent hydrocarbon radical of one to six carbon atoms substituted with one or two —COOH group e.g., carboxymethyl, 2-carboxyethyl, 3-carboxypropyl, and the like.

"Aryl" refers to an all-carbon monocyclic or fused-ring polycyclic (i.e., rings which share adjacent pairs of carbon atoms) groups of 6 to 12 carbon atoms having a completely conjugated pi-electron system. Examples, without limitation, of aryl groups are phenyl, naphthalenyl and anthracenyl. The aryl group may be substituted or unsubstituted. When substituted, the aryl group is substituted with one or more, more preferably one, two or three, even more preferably one or two substituents independently selected from the group consisting of alkyl, haloalkyl, halo, hydroxy, alkoxy, mercapto, alkylthio, cyano, acyl, nitro, phenoxy, haloalkoxy, carboxy, alkoxycarbonyl, amino, alkylamino or dialkylamino.

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, triazole, tetrazole, triazine, and carbazole. The heteroaryl group may be substituted or unsubstituted. When substituted, the heteroaryl group is substituted with one or more, more preferably one, two or three, even more preferably one or two substituents independently selected from the group consisting of alkyl, haloalkyl, halo, hydroxy, alkoxy, mercapto, alkylthio, cyano, acyl, nitro, haloalkyl, haloalkoxy, carboxy, alkoxycarbonyl, amino, alkylamino or dialkylamino.

"Heterocycle" means a saturated cyclic radical of 3 to 8 ring atoms in which one, two or three ring atoms are heteroatoms selected from N, O, or $S(O)_n$ (where n is an integer from 0 to 2), the remaining ring atoms being C, where one or two C atoms may optionally be replaced by a carbonyl group. The heterocyclyl ring may be optionally substituted independently with one or more, preferably one, two, or three substituents selected from alkyl (wherein the alkyl may be optionally substituted with one or two substituents independently selected from carboxy or alkoxycarbonyol), haloalkyl, cyanoalkyl, halo, nitro, cyano, hydroxy, alkoxy, amino, alkylamino, dialkylamino, hydroxyalkyl, carboxyalkyl, aryl, heteroaryl, aralkyl, heteroaralkyl, and —COR (where R is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof. Preferably, the heterocycle group is optionally substituted with one or two substituents independently selected from halo, alkyl, alkyl substituted with carboxy, ester, hydroxy, alkylamino, saturated or unsaturated heterocycloamino, saturated or unsaturated heterocycloaminoalkyl, or dialkylamino.

"Heterocycloamino" means a saturated or partially saturated cyclic radical of 3 to 8 ring atoms in which at least one of the ring atoms is nitrogen and optionally where one or two additionally ring atoms are heteroatoms selected from —$NR^a$— (where $R^a$ is alkyl, acyl, aryl, or heteroaryl), O, or $S(O)_n$ (where n is an integer from 0 to 2), the remaining ring atoms being C, where one or two C atoms may optionally be replaced by a carbonyl group. The heterocycloamino ring may be optionally substituted independently with one, two, or three substituents selected from alkyl, acyl, alkoxycarbonyl, hydroxyalkylcarbonyl, carboxyalkyl, alkoxycarbonylalkyl, hydroxy, hydroxyalkyl, alkoxyalkyl, alkoxy, aryl, aralkyl, heteroaralkyl, and heterocyclylalkyl. More specifically the term heterocycloamino includes, but is not limited to, piperidin1-yl, piperazin-1-yl, pyrrolidin-1-yl, 2-oxo-pyrrolidin-1-yl, 2,5-dioxo-pyrrolidin-1-yl, morpholin-4-yl, thiomorpholin-4-yl, thiomorpholino-1-oxide, thiomorpholino-1,1-dioxide, 4-ethyloxycarbonylpiperazin-1-yl, 3-oxopiperazin-1-yl, 2-imidazolidon-1-yl, 2-pyrrolidinon-1-yl, 2-oxohomopiperazino, tetrahydropyrimidin-2-one, and the derivatives thereof.

"Hydroxy" refers to an —OH group.

"Cyano" refers to a —C≡N group.

"Nitro" refers to a —$NO_2$ group.

"Aralkyl" means alkyl as defined above which is substituted with an aryl group as defined above, e.g., —$CH_2$phenyl, —$(CH_2)_2$phenyl, —$(CH_2)_3$phenyl, —$H_2$CH$(CH_3)CH_2$phenyl,and the like and derivatives thereof.

"Heteroaralkyl" group means alkyl as defined above which is substituted with a heteroaryl group, e.g., —$CH_2$pyridinyl, —$(CH_2)_2$pyrimidinyl, —$(CH_2)_3$imidazolyl, and the like, and derivatives thereof.

"Heterocyclylalkyl" group means alkyl as defined above which is substituted with a heterocycle group, e.g., —$CH_2$pyrrolidin-1-yl, —$(CH_2)_2$piperidin-1-yl, and the like, and derivatives thereof.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocyclo group is not substituted with the alkyl group.

The terms "2-indolinone","indolin-2-one" and "2-oxindole" are used interchangeably herein to refer to a molecule having the chemical structure:

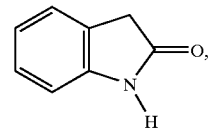

The term "pyrrole" refers to a molecule having the chemical structure:

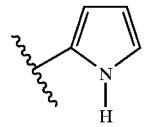

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the $R^6$ substituent in a compound of formula (I) is 2-hydroxyethyl, then the carbon to which the hydroxy group is attached is an asymmetric center and therefore the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of Formula (I) may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate RTK, CTK and/or STK activity and is not limited to any one tautomeric or structural isomeric form.

It is contemplated that a compound of Formula (I) would be metabolized by enzymes in the body of the organism such as human being to generate a metabolite that can modulate the activity of the protein kinases. Such metabolites are within the scope of the present invention.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts which retain the biological effectiveness and properties of the parent compound. Such salts include:

(1) acid addition salt which is obtained by reaction of the free base of the parent compound with inorganic acids such as hydrochloric acid, hydrobromic acid, nitric acid, phosphoric acid, sulfuric acid, and perhcloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compound of Formula (I) may also act as a prodrug. A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug"), carbamate or urea. For example, a compound of Formula (I) where $R^4$ is $-PO(OR^8)_2$, $-COR^9$, or $-CHR^{10}NR^{11}R^{12}$ where $R^9-R^{12}$ are as defined in the Summary of the Invention may convert in vivo to generate a corresponding compound of Formula (I) where $R^4$ is hydrogen.

"PK" refers to receptor protein tyrosine kinase (RTKs), non-receptor or "cellular" tyrosine kinase (CTKs) and serine-threonine kinases (STKs).

"Method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

"Modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

"Catalytic activity" refers to the rate of phosphorylation of tyrosine under the influence, direct or indirect, of RTKs and/or CTKs or the phosphorylation of serine and threonine under the influence, direct or indirect, of STKs.

"Contacting" refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium.

"In vivo" refers to procedures performed within a living organism such as, without limitation, a mouse, rat or rabbit.

"PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukariotic cell or as complex as a mammal, including dogs, cats, and human beings.

"Therapeutically effective amount" refers to that amount of the compound being administered which will relieve to some extent one or more of the symptoms of the disorder being treated. In reference to the treatment of cancer, a therapeutically effective amount refers to that amount which has the effect of:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and/or,
(4) relieving to some extent (or, preferably, eliminating) one or more symptoms associated with the cancer.

"Monitoring" means observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art.

The above-referenced effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

"Natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

Representative compounds of Formula (I) where m is 1 are shown in Table 1 below:

TABLE 1

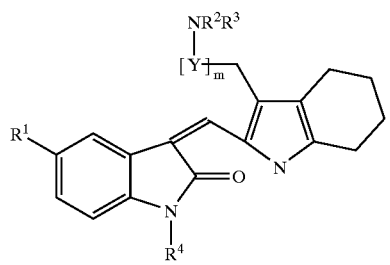

| Cpd.# | Y | $R^1$ | $R^2$ | $R^3$ | $NR^2R^3$ |
|---|---|---|---|---|---|
| 1 | —(CH$_2$)$_2$— | —SO$_2$NHCH$_3$ | —CH$_3$ | —CH$_3$ | — |
| 2 | —(CH$_2$)$_2$— | —SO$_2$NHCH$_3$ | — | — | 4-methylpiperazin-1-yl |
| 3 | —COCH$_2$— | —SO$_2$NHCH$_3$ | — | — | 4,5-dimethylpiperazin-1-yl |
| 4 | —COCH$_2$— | —SO$_2$NHCH$_3$ | — | — | 4-methylpiperazin-1-yl |
| 5 | —COCH$_2$— | —SO$_2$CH$_2$CH$_3$ | — | — | 4,5-dimethylpiperazin-1-yl |
| 6 | —COCH$_2$— | —SO$_2$CH$_2$CH$_3$ | — | — | 4-methylpiperazin-1-yl |
| 7 | —(CH$_2$)$_2$— | —SO$_2$CH$_2$CH$_3$ | — | — | 4-methylpiperazin-1-yl |
| 8 | —(CH$_2$)$_2$— | —SO$_2$NHCH$_3$ | — | — | 4-CH$_3$CH$_2$OC(O)-piperazin-1-yl |
| 9 | —(CH$_2$)$_2$— | —SO$_2$CH$_2$CH$_3$ | — | — | 4-CH$_3$CH$_2$OC(O)-piperazin-1-yl |
| 10 | —(CH$_2$)$_2$— | —SO$_2$NHCH$_3$ | — | — | 4-CH$_3$C(O)-piperazin-1-yl |
| 11 | —(CH$_2$)$_2$— | —SO$_2$CH$_2$CH$_3$ | — | — | 4-CH$_3$C(O)-piperazin-1-yl |
| 12 | —(CH$_2$)$_2$— | —SO$_2$NHCH$_3$ | — | — | 4-HC(O)-piperazin-1-yl |
| 13 | —(CH$_2$)$_2$— | —SO$_2$CH$_2$CH$_3$ | — | — | 4-HOCH$_2$C(O)-piperazin-1-yl |
| 14 | —(CH$_2$)$_2$— | —SO$_2$NHCH$_3$ | — | — | 4-HOCH$_2$C(O)-piperazin-1-yl |
| 15 | —(CH$_2$)$_2$— | —SO$_2$NHCH$_3$ | — | — | piperazin-1-yl |
| 16 | —(CH$_2$)$_2$— | —SO$_2$CH$_2$CH$_3$ | — | — | 4-HC(O)-piperazin-1-yl |
| 17 | —(CH$_2$)$_2$— | —SO$_2$NHCH$_3$ | — | — | 4-CH$_3$CH$_2$OC(O)CH$_2$-piperazin-1-yl |
| 18 | —(CH$_2$)$_2$— | —SO$_2$NHCH$_3$ | — | — | 4-HOC(O)CH$_2$-piperazin-1-yl |
| 19 | —(CH$_2$)$_2$— | —SO$_2$CH$_2$CH$_3$ | — | — | 4-HOC(O)CH$_2$-piperazin-1-yl |
| 20 | —(CH$_2$)$_2$— | —SO$_2$NHCH$_3$ | — | — | 4-HO-piperidin-1-yl |

TABLE 1-continued

| Cpd.# | Y | $R^1$ | $R^2$ | $R^3$ | $NR^2R^3$ |
|---|---|---|---|---|---|
| 21 | —(CH$_2$)$_2$— | —SO$_2$CH$_2$CH$_3$ | — | — | 4-HO-piperidin-1-yl |
| 22 | —(CH$_2$)$_2$— | —SO$_2$NHCH$_3$ | — | — | 4-HO—(CH$_2$)$_2$-piperazin-1-yl |
| 23 | —(CH$_2$)$_2$— | —SO$_2$CH$_2$CH$_3$ | — | — | 4-HO—(CH$_2$)$_2$-piperazin-1-yl |
| 24 | —(CH$_2$)$_2$— | —SO$_2$NHCH$_3$ | — | — | 3,5-dimethylpiperazin-1-yl |
| 25 | —(CH$_2$)$_2$— | —SO$_2$CH$_2$CH$_3$ | — | — | 3,5-dimethylpiperazin-1-yl |
| 26 | —(CH$_2$)$_2$— | —SO$_2$NH(CH$_2$)$_2$OH | — | — | morpholin-4-yl |
| 27 | —(CH$_2$)$_2$— | —SO$_2$NH(CH$_2$)$_2$OH | —CH$_3$ | —CH$_3$ | — |
| 28 | —(CH$_2$)$_2$— | —SO$_2$NHCH$_3$ | —CH$_3$ | —(CH$_2$)$_2$—OH | — |
| 29 | —(CH$_2$)$_2$— | —SO$_2$CH$_2$CH$_3$ | —CH$_3$ | —(CH$_2$)$_2$—OH | — |

PREFERRED EMBODIMENTS

While the broadest definition is set forth in the Summary of the Invention, in compounds of Formula (I) set forth below are preferred.

1. A preferred group of compounds is that wherein m is 1 and Y is ethylene.
2. Another preferred group of compounds is that wherein m is 1 and Y is —COCH$_2$—.
3. Yet another preferred group of compounds is that wherein m is 0.

(A) Within groups (1–3), a more preferred group of compounds is that wherein $R^4$ is hydrogen.
(i) Within the above preferred-and more preferred groups of compounds, an even more preferred group of compounds is that wherein:

$R^1$ is —SO$_2R^5$ where $R^5$ is alkyl, preferably methyl, ethyl, n or iso-propyl or n, iso-, or tert-butyl. More preferably $R^5$ is ethyl.

(ii) Within the above preferred and more preferred groups of compounds, an even more preferred group of compounds is that wherein:

$R^1$ is —SO$_2NR^6R^7$ where $R^6$ is hydrogen or alkyl, preferably hydrogen or methyl. More preferably $R^6$ is hydrogen; and $R^7$ is alkyl, cycloalkyl or hydroxyalkyl, preferably methyl, ethyl, 2-hydroxyethyl, or 3-hydroxypropyl. More preferably $R^7$ is methyl or 2-hydroxyethyl.

Within the above preferred, more preferred and even more preferred groups, particularly preferred group of compounds is that wherein:

(a) $R^2$ and $R^3$ are independently alkyl, preferably methyl, ethyl or propyl, more preferably methyl;
(b) $R^2$ is hydrogen or alkyl; preferably methyl; and $R^3$ is hydroxyalkyl, preferably 2-hydroxyethyl, hydroxypropyl (including all isomers), more preferably 2-hydroxyethyl; or
(c) $R^2$ and $R^3$ together with the nitrogen atom to which they are attached form heterocycloamino, preferably morpholin-4-yl, pyrrolidin-1-yl, piperidin-1-yl, or piperazin-1-yl wherein said rings are optionally substituted with one or two substituents independently selected from alkyl, alkoxycarbonyl, acyl, hydroxyalkylcarbonyl, alkoxycarbonylalkyl, carboxyalkyl, hydroxy, or hydroxyalkyl. Preferably $R^2$ and $R^3$ together with the nitrogen atom to which they are attached form 4-methylpiperazin-1-yl, 3,5-dimethylpiperazin-1-yl, 4-ethyloxycarbonylpiperazin-1-yl, 4-acetylpiperazin-1-yl, 4-formylpiperazin-1-yl, 4-hydroxymethylcarbonyl-piperazin-1-yl, piperazin-1-yl, 4-ethoxycarbonylmethylpiperazin-1-yl, 4-carboxymethylpiperazin-1-yl, 4-hydroxypiperidin-1-yl, 4-(2-hydroxyethyl)piperazin-1-yl, or morpholin-4-yl.

(B) Within groups (1–3), another more preferred group of compounds is that wherein $R^4$ is hydrogen; and
(a) $R^2$ and $R^3$ are independently alkyl, preferably methyl, ethyl or propyl, more preferably methyl;
(b) $R^2$ is hydrogen or alkyl; preferably methyl; and $R^3$ is hydroxyalkyl, preferably 2-hydroxyethyl, hydroxypropyl (including all isomers), more preferably 2-hydroxyethyl; or
(c) $R^2$ and $R^3$ together with the nitrogen atom to which they are attached form heterocycloamino, preferably morpholin-4-yl, pyrrolidin-1-yl, piperidin-1-yl, or piperazin-1-yl wherein said rings are optionally substituted with one or two substituents independently selected from alkyl, alkoxycarbonyl, acyl, hydroxyalkylcarbonyl, alkoxycarbonylalkyl, carboxyalkyl, hydroxy, or hydroxyalkyl. Preferably $R^2$ and $R^3$ together with the nitrogen atom to which they are attached form 4-methylpiperazin-1-yl, 3,5-dimethylpiperazin-1-yl, 4-ethyloxycarbonylpiperazin-1-yl, 4-acetylpiperazin-1-yl, 4-formylpiperazin-1-yl, 4-hydroxymethylcarbonyl-piperazin-1-yl, piperazin-1-yl, 4-ethoxycarbonylmethylpiperazin-1-yl, 4-carboxymethylpiperazin-1-yl, 4-hydroxypiperidin-1-yl, 4-(2-hydroxyethyl)piperazin-1-yl, or morpholin-4-yl.

General Synthesis

Compounds of Formula (I) can be prepared by the method described in Scheme A below:

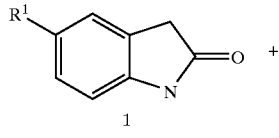

1

Compounds of Formula (I) where $R^4$ is hydrogen can be readily prepared by condensing an 2-indolinone of formula 1 where $R^1$ is as defined in the Summary of the Invention with a 4,5,6,7-tetrahydro-1H-indole-2-carbaldehyde of formula 2 where m, Y, $R^2$ and $R^3$ are as defined in the Summary of the Invention. The reaction is carried out in the presence of an organic base such as piperidine, pyridine, trethylamine, diisopropylethylamine, and the like and in an alcoholic solution such as ethanol, propanol, and the like. In some cases heating the reaction mixture may be necessary.

Compounds of formula 1 can be prepared by methods well known in the art. For example compounds of formula 1 where $R^1$ is —$SO_2NR^6R^7$ can be prepared by the methods disclosed in PCT Application Publication No. WO 98/50356. Compounds of formula 1 where $R^1$ is —$SO_2R^5$ can be prepared from 5-chlorosulfonyl-2-indolinone (synthesis described WO 98/50356) as described in working Example 5 below.

Compounds of formula 2 can be prepared by methods well known in the art. For example, compounds of formula 2 can be prepared from 3-(4-oxo-4,5,6,7-tetrahydro-1H-indol-3-yl)propionic acid as described in Examples 1–29 below.

A compound of Formula (I) where $R^4$ is hydrogen can be converted to a corresponding compound of Formula (I) where $R^4$ is —$PO(OR^8)_2$, —$COR^9$, or —$CHR^{10}NR^{11}R^{12}$ where $R^8$, $R^9$, $R^{10}$, $R^{11}$ and $R^{12}$ are as defined in the Summary of the Invention by methods well known in the art. Some such methods are described below.

Compounds of Formula (I) where $R^4$ is —$P(O)(OR^8)_2$ where $R^8$ are not hydrogen can be prepared by reacting (I) where $R^4$ is hydrogen with a phosphorylating agent such as phosphoryl halide e.g., dimethyl chlorophosphate. The reaction is carried out in the presence of a strong base such as sodium hydride and in an organic solvent such as THF, DMF, and the like. The methyl groups can be removed under suitable demethylation reaction conditions such as treatment with N,O-bis(trimethylsilyl)acetamide in the presence of trimetylsilylbromide to provide a compound of Formula (I) where $R^8$ are hydrogen. The reaction is typically carried out in a polar organic solvent such as acetonitrile.

Compounds of Formula (I) where $R^4$ is —$COR^9$ where $R^9$ is as defined in the Summary of the Invention can be readily prepared by acylating a compound of Formula (I) where $R^4$ is hydrogen with a suitable acylating agent e.g., carboxylic acid anhydrides such as acetic anhydride, succinic anhydride, carboxylic acid chlorides such as acetyl chloride, butryl chloride, and the like or carboxylic acid active esters. The reaction may be carried out in the presence of an organic base, preferably a tertiary nitrogen base. Examples of tertiary nitrogen bases include, but are not limited to, trimethylamine, triethylamine, pyridine, and 1,8-diazabicyclo[5.4.1]undec-7-ene.

The solvent in which the reaction is carried out may be an aprotic solvent. A "protic solvent" is a solvent which has hydrogen atom(s) covalently bonded to oxygen or nitrogen atoms which renders the hydrogen atoms appreciably acidic and thus capable of being "shared" with a solute through hydrogen bonding. An "aprotic solvent" may be polar or non-polar but, in either case, does not contain acidic hydrogens and therefore is not capable of hydrogen bonding with solutes. Examples, without limitation, of non-polar aprotic solvents, are pentane, hexane, benzene, toluene, methylene chloride and carbon tetrachloride. Examples of polar aprotic solvents are chloroform, tetrahydrofuran, dimethylsulfoxide, dimethylformamide and pyridine. In a presently preferred embodiment of this invention, the solvent is a polar aprotic protic solvent, preferably dimethylformamide, tetrahydrofuran or pyridine. The reaction is typically carried out at room temperature.

Finally, compounds of Formula (I) where $R^4$ is —$CHR^{10}NR^{11}R^{12}$ where $R^8$, $R^9$, $R^{10}$, $R^{11}$ and $R^{12}$ are as defined in the Summary of the Invention can be prepared by reacting a compound of Formula (I) where $R^4$ is hydrogen with an aldehyde such as formaldehyde, acetaldehyde, and the like, and a suitable amine.

The solvent in which the reaction is carried out may be a protic or an aprotic solvent, preferably it is a protic solvent such as an alcohol e.g., methanol or ethanol, or an aqueous alcohol. The reaction may be carried out at temperatures greater than room temperature. The temperature is generally from about 20° C. to about 100° C., preferably about 40° C. to about 80° C. By "about" is meant that the temperature range is preferably within 10 degrees Celsius of the indicated temperature, more preferably within 5 degrees Celsius of the indicated temperature and, most preferably, within 2 degrees Celsius of the indicated temperature. Thus, for example, by "about 60° C." is meant 60° C.±10° C., preferably 60° C.±5° C. and most preferably, 60° C.±2° C.

Suitable amines include alicyclic and cyclic secondary amines. These amines are either commercially available from Aldrich, Sigma, etc., or they can be prepared by methods well known in the art. Exemplary secondary amines include dimethylamine, diethylamine, methylamine, ethylamine, and diisopropylamine. Exemplary cyclic secondary amines include piperazine, 3,5-dimethylpiperazine, proline, morpholine, thiomorpholine, 2-hydroxymethylpyrrolidne, and pyrrolidine.

Utility

The compounds of Formula (I) are inhibitors of Src family of kinases, in particular, Src kinase. Hence the compounds of Formula (I) are useful in treating diseases such as cancers, in particular colon tumors, endometrial cancer, breast, ovarian, colon, pancreatic, head and neck squamous cell carcinoma, hepatocellular carcinoma and bladder tumors. The compounds of the present invention are also useful in treating bone disorders such as osteoporosis. The compounds of the present invention also inhibit other kinases such as Yes, Lck, Lyn, EGF, Met, HER2, HER3, HER4, IR, IGF-1R, IRR, PDGFRα, PDGFRβ, CSFIR, C-Kit, C-fms, Flk-1R, Flk4, KDR/Flk-1, Flt-1, Flt3, FGFR-1R, FGFR-2R, FGFR-3R, FGFR-4R, Frk, Btk, Csk, Abl, ZAP70, Fes/Fps, Fak, Jak, Ack, Blk, Hck, Fgr, Yrk, CDK2 and Raf. Hence these compounds are useful in various diseases mediated by these kinases see., U.S. Pat. No. 5,792,783, the disclosure of which is hereby incorporated by reference in its entirety.

Testing

The ability of the compounds of this invention to inhibit Src kinase can be tested by the methods described in biological examples below. The ability of the compounds of formula (I) to inhibit other kinases can be measured by the assays described in U.S. Pat. No. 5,792,783, the disclosure of which is hereby incorporated by reference in its entirety.

Administration and Pharmaceutical Composition

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

As used herein, "administer" or "administration" refers to the delivery of a compound of Formula (I) or a pharmaceutically acceptable salt thereof or of a pharmaceutical composition containing a compound of Formula (I) or a pharmaceutically acceptable salt thereof of this invention to an organism for the purpose of prevention or treatment of a PK-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are oral and intravenous.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

Pharmaceutical compositions which may also be used include hard gelatin capsules. As a non-limiting example, the active compound capsule oral drug product formulation may be as 50 and 200 mg dose strengths (formulation codes J-011248-AA-00 and J-011248-AA-01, respectively). The two dose strengths are made from the same granules by filling into different size hard gelatin capsules, size 3 for the 50 mg capsule and size 0 for the 200 mg capsule. The composition of the formulation may be, for example, as indicated in Table 2.

TABLE 2

| Ingredient Name/Grade | Concentration in Granulation (% w/w) | Amount in 50 mg Capsule (mg) | Amount in 200 mg Capsule (mg) |
|---|---|---|---|
| Active Compound NF | 65.0 | 50.0 | 200.0 |
| Mannitol NF | 23.5 | 18.1 | 72.4 |
| Croscarmellose sodium NF | 6.0 | 4.6 | 18.4 |
| Povidone K 30 NF | 5.0 | 3.8 | 15.2 |
| Magnesium stearate NF | 0.5 | 0.38 | 1.52 |
| Capsule, Swedish yellow NF | | Size 3 | Size 0 |

The capsules may be packaged into brown glass or plastic bottles to protect the active compound from light. The containers containing the active compound capsule formulation must be stored at controlled room temperature (15–30° C.).

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the fomulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharamcologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide ($Ca(OH)_2$), etc.).

Pharmaceutical compositions suitable for use in the present invention include compositions wherein the active ingredients are contained in an amount sufficient to achieve the intended purpose, e.g., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%.

At present, the therapeutically effective amounts of compounds of Formula (I) may range from approximately 25 mg/m$^2$ to 1500 mg/m$^2$ per day; preferably about 3 mg/m$^2$/day. Even more preferably 50mg/qm qd till 400 mg/qd.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

It is also an aspect of this invention that a compound described herein might be combined with other chemotherapeutic agents for the treatment of the diseases and disorders discussed above. For instance, a compound, salt or prodrug of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan, improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethio-phosphoramide and trimethylolmelamine; and the nitrogen mustards, e.g., chlorambucil, cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines.

A compound of this invention can also be used in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

It is contemplated that a compound of this invention can also be used in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound of this invention could also be used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors such as anastrozole.

Finally, it is also contemplated that the combination of a compound of this invention will be effective in combination with Endostatin®, Gleevec®, Camptosar®, Herceptin®, Imclone C225, mitoxantrone or paclitaxel. The compounds of this invention can also be used with a COX-2 selective inhibitor such as Celecoxib, Paracoxib, Valecoxib, Rofecoxib, Vioxx, Japan Tobacco JTE-522, MK633, and Novartis's Cox 189. The COX-2 selective inhibitors used in the therapeutic combinations of the present invention can be prepared in the manner set forth in U.S. Pat. No. 5,466,823, U.S. Pat. No. 5,633,272; U.S. Pat. No. 5,932,598; U.S. Pat. No. 5,968,974; JP90/52,882; and WO 99/11605.

The phrase "combination therapy" (or "co-therapy") embraces the administration of a compound of Formula (I) with other neoplastic agent as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" generally is not intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, both the therapeutic agents may be administered orally or both therapeutic agents may be administered by intravenous injection. The sequence in which the therapeutic agents are administered is not narrowly critical.

"Combination therapy" also can embrace the administration of the therapeutic agents as described above in further combination with other biologically active ingredients (such as, but not limited to, a second and different antineoplastic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

Determination of a therapeutically effective amount of a compound of Formula (I) with other neoplastic agent(s) for use in the combination therapy is well within the capability of those skilled in the art.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

Example 1

Synthesis of 3-[1-[3-(3-dimethylaminopropyl)-4,5,6,7-tetrahydro-1H-indol-2-yl]-meth-(Z)-ylidene]-2-oxo-2,3-dihydro-1H-indole-5-sulfonic acid methylamide

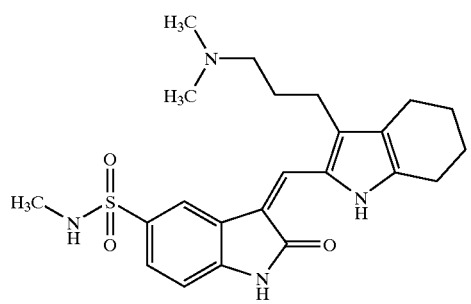

Step 1:
5-Aminolevulinic acid hydrochloride salt (13.7 g, 0.1 mol), sodium acetate (41 g, 0.2 mol), and 1,2-cyclohexanedione (11.2 g, 0.1 mol) were stirred for 20 hours in 200 ml of water at 50° C. The mixture was cooled and the solid product collected by vacuum filtration and washed with 50% ethanol in water. The product was slurry-washed in 100 ml of 50% ethanol in water, collected and dried under vacuum to give 3-(4-oxo-4,5,6,7-tetrahydro-1H-indol-3-yl) propionic acid (12 g, 67% yield).

Step 2:
3-(4-Oxo-4,5,6,7-tetrahydro-1H-indol-3-yl)-propionic acid (12 g, 0.06 mol) was suspended in 80 ml of dichloromethane and carbonyldiimidazole (11.3 g, 0.07 mol) was added with stirring. After 30 minutes 58 ml of 2.0 M dimethylamine in tetrahydrofuran was added. After one hour the solvent was rotary evaporated. The residue was redissolved in dichloromethane, washed with 1 N hydrochloric acid and brine, dried over anhydrous magnesium sulfate and rotary evaporated. The solid residue was washed with ethyl acetate and dried under vacuum to give N, N-dimethyl-3-(4-oxo-4,5,6,7-tetrahydro-1H-indol-3-yl)-propionamide (8 g, 60% yield).

Step 3:

N,N-Dimethyl-3-(4-oxo-4,5,6,7-tetrahydro-1H-indol-3-yl)-propionamide (8 g, 0.034 mol) was suspended in 125 ml of tetrahydrofuran and lithium aluminum hydride (5.2 g, 0.136 mol) was slowly added. The mixture was refluxed over night, cooled in ice, and 5 ml of water and then 5 ml of 15% sodium hydroxide solution was slowly added. The mixture was stirred for 45 minutes. Water (15 ml) and sodium sulfate were added and the mixture filtered to remove solids. The solids were washed with ethyl acetate and the filtrate was concentrated to give dimethyl-[3-(4,5,6,7-tetrahydro-1H-indol-3-yl)-propyl]-amine (6.3 g, 90% yield).

Step 4:

Phosphorus oxychloride (9.2 g, 0.06 mol) was slowly added to 12 ml of dimethylformamid at 0° C. with stirring and the mixture stirred for 30 minutes. Dimethyl-[3-(4,5,6,7-tetrahydro-1H-indol-3-yl)-propyl]-amine ( 6.2 g, 0.03 mol) was dissolved in 10 ml of dimethylformamide and added to the mixture. The reaction was stirred for 2 hours at room temperature. The stirred mixture was cooled in an ice bath and water was slowly added followed by 10 N sodium hydroxide solution until pH was 10. The mixture was stirred at room temperature for 45 minutes and extracted with ethyl acetate. The ethyl acetate extract was washed with brine, dried over anhydrous sodium sulfate and concentrated to give 3-(3-dimethylamino-propyl)-4,5,6,7-tetrahydro-1H-indole-2-carbaldehyde (3.5 g, 50% yield).

Step 5:

3-(3-Dimethylaminopropyl)-4,5,6,7-tetrahydro-1H-indole-2-carbaldehyde (71 mg, 0.3 mmol), 5-methylaminosulfonyloxindole (68 mg, 0.3 mmol) and piperidine (0.03 ml) in 1 ml of ethanol was stirred at 60° C. for over night. The mixture was cooled and the solids collected by vacuum filtration and washed with ethanol to give (93 mg, 70% yield) of 3-[1-[3-(3-dimethylaminopropyl)-4,5,6,7-tetrahydro-1H-indol-2-yl]-meth-(Z)-ylidene]-2-oxo-2,3-dihydro-1H-indole-5-sulfonic acid methylamide.

Example 2

Synthesis of 3-[1-{3-[3-(4-methyl-piperazin-1-yl)-propyl]-4,5,6,7-tetrahydro-1H-indol-2-yl}-meth-(Z)-ylidene]-2-oxo-2,3-dihydro-1H-indole-5-sulfonic acid methylamide

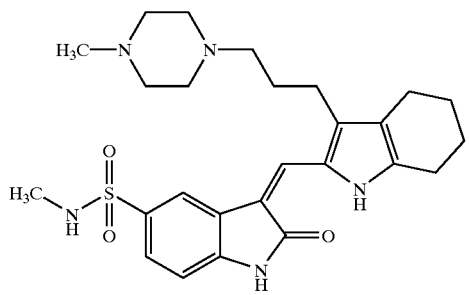

Step 1:

3-[3-(4-Methylpiperazin-1-yl)-propyl]-4,5,6,7-tetrahydro-1H-indole-2-carbaldehyde was prepared following the procedure described for 3-(3-dimethylamino-propyl)-4,5,6,7-tetrahydro-1H-indole-2-carbaldehyde as described for Example 1 above but substituting 1-methylpiperazine in step 2 above for dimethylamine.

Step 2:

3-[3-(4-Methyl-piperazin-1-yl)-propyl]-4,5,6,7-tetrahydro-1H-indole-2-carbaldehyde (87 mg, 0.3 mmol) was condensed with 5-methylaminosulfonyloxindole (68 mg, 0.3 mmol) following the same procedure used in Example 1, step 5 above. No solid precipitated out. The reaction solution was rotary evaporated and purified by flash chromatography and eluting with (dichloromethane: methanol 13/1, 10/1, 8/1) to give (70 mg, 47% yield) of 3-[1-{3-[3-(4-methyl-piperazin-1-yl)-propyl]-4,5,6,7-tetrahydro-1H-indol-2-yl}-meth-(Z)-ylidene]-2-oxo-2,3-dihydro-1H-indole-5-sulfonic acid methylamide.

Example 3

Synthesis of 3-[1-{3-[3-(3,5-dimethyl-piperazin-1-yl)-3-oxo-propyl]-4,5,6,7-tetrahydro-1H-indol-2-yl}-meth-(Z)-ylidene]-2-oxo-2,3-dihydro-1H-indole-5-sulfonic acid methylamide

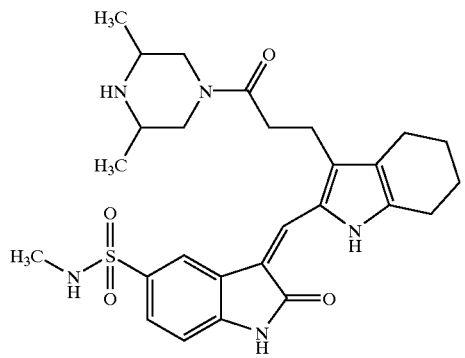

Step 1:

[3-(2-Formyl-4,5,6,7-tetrahydro-1H-indol-3-yl)-propionic acid (1.1 g, 5 mmol) was stirred for 20 minutes in 30 ml of acetonitrile followed by the addition of anhydrous1-hydroxybenzotriazole (1.62 g, 12 mmol), 2,6-dimethylpiperazine (0.684 mg, 6 mmol) and 1,3-dicyclohexylcarbodiimide (2.48 g, 12 mmol). The black-brown mixture was sonicated to dissolve most of the solid then the mixture was stirred at room temperature over night.

Thin layer chromatography (20% Methanol/dichloromethane) showed some of the starting material. The mixture was stirred at room temperature over the weekend. The reaction solution was evaporated, purified by flash chromatography and eluting with (dichloromethane: methanol 20/1, 10/1, 5/1) to give 3-[3-(3,5-dimethyl-piperazin-1-yl)-3-oxo-propyl]-4,5,6,7-tetrahydro-1H-indole-2-carbaldehyde (1.0 g) with 63% purity. The product was repurified by flash chromatography and eluting with (dichloromethane: methanol 15/1, 10/1, 5/1) to give 3-[3-(3,5-dimethylpiperazin-1-yl)-3-oxo-propyl]-4,5,6,7-tetrahydro-1H-indole-2-carbaldehyde (714 mg, 64% yield).

Step 2:

3-[3-(3,5-Dimethylpiperazin-1-yl)-3-oxo-propyl]-4,5,6,7-tetrahydro-1H-indole-2-carbaldehyde (136 mg, 0.3 mmol) was condensed with 5-methylaminosulfonyloxindole (68 mg, 0.3 mmol) following the same procedure used in Example 1 above to give 3-[1-{3-[3-(3,5-dimethyl-piperazin-1-yl)-3-oxo-propyl]-4,5,6,7-tetrahydro-1H-indol-2-yl}-meth-(Z)-ylidene]-2-oxo-2,3-dihydro-1H-indole-5-sulfonic acid methylamide (97 mg, 62% yield).

Example 4

Synthesis of 3-[1-{3-[3-(4-methyl-piperazin-1-yl)-3-oxo-propyl]-4,5,6,7-tetrahydro-1H-indol-2-yl}-meth-(Z)-ylidene]-2-oxo-2,3-dihydro-1H-indole-5-sulfonic acid methylamide

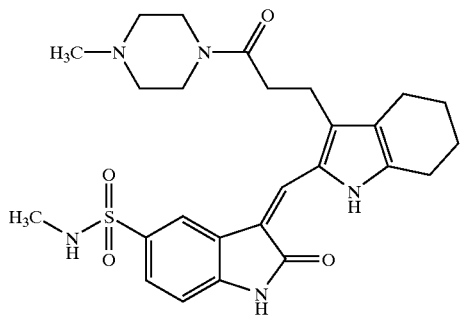

Step 1:

1-(3-Dimethylaminopropyl)-3-ethylcarbodiimide-hydrochloide (1.34 g, 7 mmol), anhydrous 1-hydroxybenzotriazole (0.95 g, 7 mmol), triethylamine(1.0 ml, 7.5 mmol) and N-methylpiperazine (664 µl, 6 mmol) were added to a mixture of [3-(2-formyl-4,5,6,7-tetrahydro-1H-indol-3-yl)-propionic acid] (1.1 g, 5 mmol) in 20 ml of N,N-dimethylformamide. The reaction was stirred at room temperature overnight. Thin layer chromatography (methanol: dichloromethane 5:1) showed one major spot. The reaction solution was concentrated under high vacuum over night then the residue was purified by flash chromatography and eluting with (dichloromethane: methanol 15/1, 10/1, 5/1) to give 3-[3-(4-methyl-piperazin-1-yl)-3-oxo-propyl]-4,5,6,7-tetrahydro-1H-indole-2-carbaldehyde (1.18 g, 78% yield).

Step 2:

3-[3-(4-Methylpiperazin-1-yl)-3-oxo-propyl]-4,5,6,7-tetrahydro-1H-indole-2-carbaldehyde (121 mg, 0.3 mmol) was condensed with 5-methylaminosulfonyl-oxindole (68 mg, 0.3 mmol) following the same procedure used in Example 1 to give the desired product (86 mg, 56% yield).

Example 5

Synthesis of 3-[1-{3-[3-(3,5-dimethyl-piperazin-1-yl)-3-oxo-propyl]-4,5,6,7-tetrahydro-1H-indol-2-yl}-meth-(Z)-ylidene]-5-ethanesulfonyl-1,3-dihydro-indol-2-one

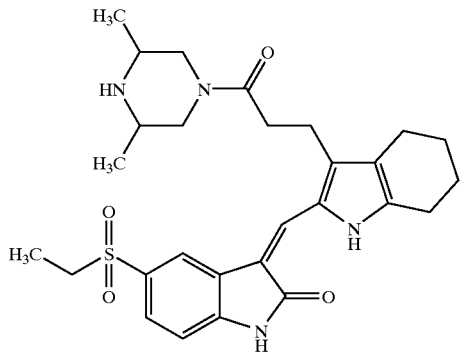

Step 1:

To a suspension of 5-chlorosulfonyloxindole (30 g, 129.9 mmol) (see *J. Med. Chem.*, 42, 23, 1999, 4890–4908) in THF: water (2:1) (645 ml) (0.2M) was added to a presonicated (15 minutes) suspension Zn dust (90% purity, 8.4 g, 129.9 mmol) portionwise. The mixture was stirred at 25° C. for 18 hours. TLC showed the complete disappearance of the starting material. The reaction mixture was concentrated to one quarter the reaction volume where the solid product was filtered, and washed repeatedly with water to remove zinc chloride. After high vacuum dry, 5-zinc sulfinate-1,3-dihydro-indol-2-one (32.4 g, 55%) was obtained as an off white solid.

Step 2:

To a suspension of 5- zinc sulfinate-1,3-dihydro-indol-2-one (1 molar equivalent) in THF: water (2:1) (0.2 M) was added ethyliodide (2.2 molar equivalents). The mixture was stirred at 70° C. (oil bath) for 24–48 hours. After TLC judged the reaction to be complete. The mixture was cooled to room temperature, diluted with ethyl acetate, and separated from water layer. The ethyl acetate solution was further washed with water and separated after which time the solvents were evaporated, and the product precipitated out it was filtered, washed with diethyl ether, and dried under high vacuum to provide 5-ethylsulfonyloxindole as an orange-red solid.

Step 3:

3-[3-(3,5-Dimethylpiperazin-1-yl)-3-oxo-propyl]-4,5,6,7-tetrahydro-1H-indole-2-carbaldehyde, prepared as described in Example 3 above, was condensed with 5-ethylsulfonyloxindole following the same procedure used in example 1 to give the desired product (72 mg, 46% yield).

Example 6

Synthesis of 5-ethanesulfonyl-3-[1-{3-[3-(4-methyl-piperazin-1-yl)-3-oxo-propyl]-4,5,6,7-tetrahydro-1H-indol-2-yl}-meth-(Z)-ylidene]-1,3-dihydro-indol-2-one

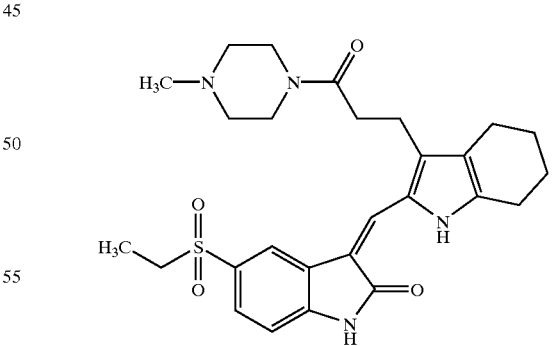

3-[3-(4-Methylpiperazin-1-yl)-3-oxo-propyl]-4,5,6,7-tetrahydro-1H-indole-2-carbaldehyde, prepared as described in Example 4 above, was condensed with 5-ethylsulfonyloxindole (see Example 5) following the same procedure used in Example 1 to provide the desired product (80 mg, 53%).

Example 7

Synthesis of 5-ethanesulfonyl-3-[1-{3-[3-(4-methyl-piperazin-1-yl)-propyl]-4,5,6,7-tetrahydro-1H-indol-2-yl}-meth-(Z)-ylidene]-1,3-dihydro-indol-2-one

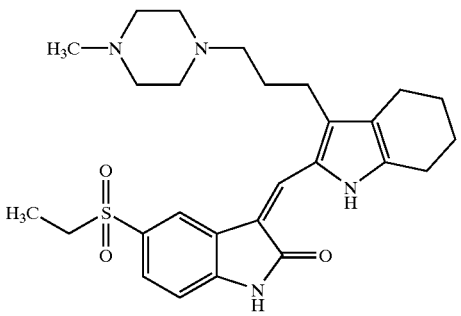

3-[3-(4-Methylpiperazin-1-yl)-propyl]-4,5,6,7-tetrahydro-1H-indole-2-carbaldehyde, prepared as described in Example 2, was condensed with 5-ethylsulfonyloxindole (Example 5) following the procedure described in Example 1 above. The reaction mixture was purified by flash chromatography and eluting with (dichloromethane: methanol 30/1, 20/1, 15/1) to give the desired product.

Example 8

Synthesis of 4-(3-{2-[5-methylsulfamoyl-2-oxo-1,2-dihydro-indol-(3Z)-ylidenemethyl]-4,5,6,7-tetrahydro-1H-indol-3-yl}-propyl)-piperazine-1-carboxylic acid ethyl ester

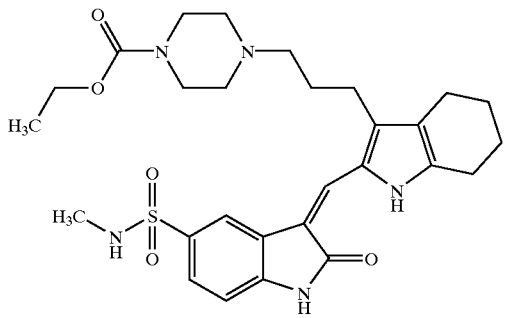

Step 1:

3-(4-Oxo-4,5,6,7-tetrahydro-1H-indol-3-yl)-propionic acid (2.07 g, 10 mmol), prepared as described in Example 1 above, 1-(3-dimethylaminopropyl)-3-ethylcarbodiimide-hydrochloide (2.3 g, 12 mmol), anhydrous 1-hydroxybenzotriazole (1.62 g, 12 mmol) and N,N-diisopropylethylamine (1.75 ml, 10 mmol) were mixed together in 50 ml of dichloromethane and stirred for one hour at room temperature. Tert-butyl 1-piperazinecarboxylate (2.24 g, 12 mmol) was added to the mixture and stirred at room temperature overnight. The reaction mixture was concentrated and the syrup was dissolved in dichloromethane then purified by flash chromatography, eluting with dichloromethane followed by (dichloromethane: methanol 50/1, 30/1) to give 4-[3-(4-oxo-4,5,6,7-tetrahydro-1H-indol-3-yl)-propionyl]-piperazine-1-carboxylic acid tert-butyl ester (4.45 g, 86% pure).

Step 2:

4-[3-(4-Oxo-4,5,6,7-tetrahydro-1H-indol-3-yl)-propionyl]-piperazine-1-carboxylic acid tert-butyl ester (37.5mg, 0.1 mmol) was added to 3 ml of dichloromethane at 0° C. followed by the addition of 1 ml of 20% trifluoroacetic acid. The reaction mixture was stirred at room temperature for 8 hours. The reaction solution was rotary evaporated and diluted with 1,4-dioxane. The reaction solution was concentrated at 30° C. till dryness then purified by flash chromatography and eluting with (chloroform: methanol: ammonia 20/1/0.1, 15/1/0.1) to provide 3-(3-oxo-3-piperazin-1-yl-propyl)-1,5,6,7-tetrahydro-indol-4-one.

Step 3:

3-(3-Oxo-3-piperazin-1-yl-propyl)-1,5,6,7-tetrahydro-indol-4-one (3.8 g, 75% pure) was dissolved in 1,4-dioxane (4×50 ml) and was added to a mixture of lithium aluminum hydride (3.9 g, 7 equiv.) in 50 ml of tetrahydrofuran at 0° C. The reaction mixture was refluxed at 70° C. overnight. Thin layer chromatography (dichloromethane: methanol: ammonia 5:1:0.1) showed one major spot. The reaction mixture was quenched by DI water (6 ml), 10% sodium hydroxide (14 ml) and DI water (15 ml). The formed solid was filtered out and washed twice with 1,4-dioxane. The filtrate was concentrated and dried under high vacuum to give 3-(3-piperazin-1-yl-propyl)-4,5,6,7-tetrahydro-1H-indole (2.3 g, 79% pure).

Step 4:

Phosphorus oxychloride (0.89 ml, 9.57 mmol) was slowly added to 2.03 ml of dimethylformamide at 0° C. with stirring and the mixture stirred for 30 minutes. 3-(3-Piperazin-1-ylpropyl)-4,5,6,7-tetrahydro-1H-indole (2.15 g, 8.7 mmol) was dissolved in 8 ml of dimethylformamide and added to the mixture. The reaction was stirred for 3 hours at room temperature. The stirred mixture was cooled in an ice bath and the reaction was quenched by 10 N sodium hydroxide solution until pH was >12. The reaction was stirred at room temperature for an hour then rotary evaporated at 30° C. The residue was dried under high vacuum overnight. The formed solid was purified by flash chromatography and eluting with (chloroform/methanol/ammonia solution 100/10/1, 100/13/1.3, 100/15/1.5) to provide (0.6 g, 42% yield) of 3-(3-piperazin-1-yl-propyl)-4,5,6,7-tetrahydro-1H-indole-2-carbaldehyde and 0.36 g (21% yield) of 3-[3-(4-Formyl-piperazin-1-yl)-propyl]-4,5,6,7-tetrahydro-1H-indole-2-carbaldehyde.

Step 5:

Triethylamine (146 μl, 1.0 mmol) was added to 3-(3-piperazin-1-yl-propyl)-4,5,6,7-tetrahydro-1H-indole-2-carbaldehyde (192 mg, 0.7 mmol) in 5 ml of dimethylformamide at 0° C. Ethyl chloroformate (87 μl, 0.91 mmol) was dropped in the mixture. The reaction mixture was stirred at 0° C. which was raised slowly to room temperature over night. Thin layer chromatography (dichloromethane: methanol 10:1) showed on major spot. The solvent was evaporated then the residue was purified by flash chromatography and eluting with (dichloromethane/methanol =50/1, 40/1, 30/1) to give 130 mg of 4-[3-(2-formyl-4,5,6,7-tetrahydro-1H-indol-3-yl)-propyl]-piperazine-1-carboxylic acid ethyl ester.

Step 6:

4-[3-(2-Formyl-4,5,6,7-tetrahydro-1H-indol-3-yl)-propyl]-piperazine-1-carboxylic acid ethyl ester (65 mg, 0.187 mmol) was condensed with 5-methylaminosulfonyloxindole (43 mg, 1.01 eq.) following the same condition used in Example 1 above. The precipitated solid was purified by flash chromatography, eluting with dichloromethan/methanol (50/1, 40/1, 30/1) to provide 65 mg of the desired product.

Example 9

Synthesis of 4-(3-{2-[5-Ethanesulfonyl-2-oxo-1,2-dihydro-indol-(3Z)-ylidenemethyl]-4,5,6,7-tetrahydro-1H-indol-3-yl}-propyl)-piperazine-1-carboxylic acid ethyl ester

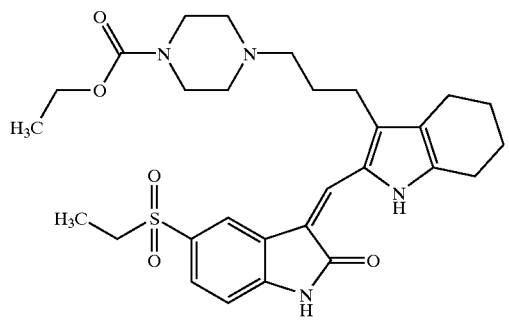

4-[3-(2-Formyl-4,5,6,7-tetrahydro-1H-indol-3-yl)-propyl]-piperazine-1-carboxylic acid ethyl ester (65 mg, 0.187 mmol), prepared as described in Example 8, was condensed with 5-ethylsulfonyloxindole (61 mg, 1.01 eq.) give the desired product.

Example 10

Synthesis of 3-[1-{3-[3-(4-acetyl-piperazin-1-yl)-propyl]-4,5,6,7-tetrahydro-1H-indol-2-yl}-meth-(Z)-ylidene]-2-oxo-2,3-dihydro-1H-indole-5-sulfonic acid methylamide

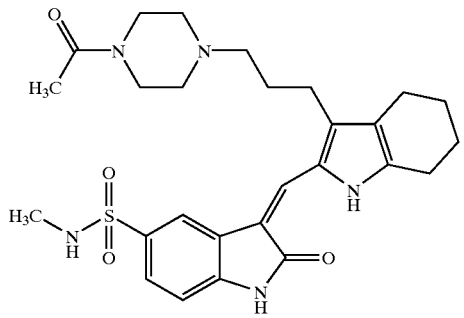

Step 1:

3-[3-(4-Acetyl-piperazin-1-yl)-propyl]-4,5,6,7-tetrahydro-1H-indole-2-carbaldehyde was prepared as described for 4-[3-(2-Formyl-4,5,6,7-tetrahydro-1H-indol-3-yl)-propyl]-piperazine-1-carboxylic acid ethyl ester in Example 8 but substituting ethyl chloroformate with with acetic anhydride.

Step 2:

3-[3-(4-Acetyl-piperazin-1-yl)-propyl]-4,5,6,7-tetrahydro-1H-indole-2-carbaldehyde (70 mg, 0.22 mmol) was condensed with 5-methylaminosulfonyl-oxindole (50 mg, 1.01eq.) under the same conditions used in Example 1 to give 61 mg of the desired product.

Example 11

Synthesis of 3-[1-{3-[3-(4-acetylpiperazin-1-yl)-propyl]-4,5,6,7-tetrahydro-1H-indol-2-yl}-meth-(Z)-ylidene]-5-ethanesulfonyl-1,3-dihydro-indol-2-one

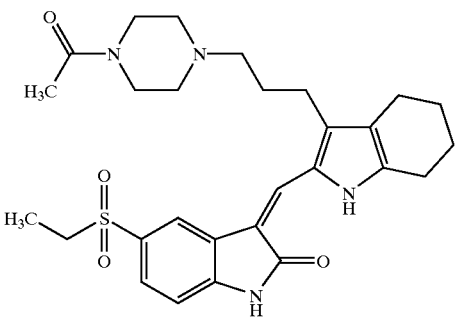

3-[3-(4-Acetyl-piperazin-1-yl)-propyl]-4,5,6,7-tetrahydro-1H-indole-2-carbaldehyde (70 mg, 0.22 mmol), prepared as described in Example 10 above, was condensed with 5-ethylsulfonyloxindole (69.5 mg, 1.01 eq, 72% pure) following the procedure used in Example 1 above. The formed solid was purified by flash chromatography using (dichloromethane: methanol 50/1, 30/1) to give 75 mg of the desired product.

Example 12

Synthesis of 3-[1-{3-[3-(4-Formyl-piperazin-1-yl)-propyl]-4,5,6,7-tetrahydro-1H-indol-2-yl}-meth-(Z)-ylidene]-2-oxo-2,3-dihydro-1H-indole-5-sulfonic acid methylamide

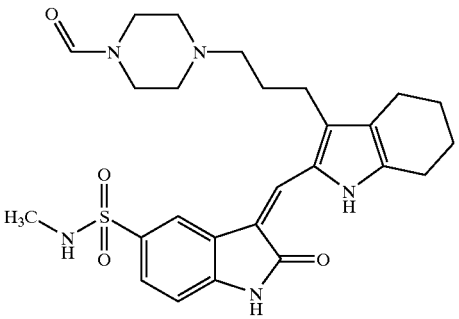

3-[3-(4-Formylpiperazin-1-yl)-propyl]-4,5,6,7-tetrahydro-1H-indole-2-carbaldehyde (61 mg, 0.2 mmol), prepared as described in Step 4 of Example 8, was condensed with 5-methylaminosulfonyloxindole (45 mg, 0.2 mmol) following the procedure used in Example 1. Brown solid precipitated out and purified by flash chromatography, eluting with (dichloromethane: methanol 50/1,35/1,30/1) to give 67 mg of the desired product.

Example 13

Synthesis of 3-[1-(3-{3-[4-(2-Hydroxy-acetyl)-piperazin-1-yl]-propyl}-4,5,6,7-tetrahydro-1H-indol-2-yl)-meth-(Z)-ylidene]-2-oxo-2,3-dihydro-1H-indole-5-sulfonic acid methylamide

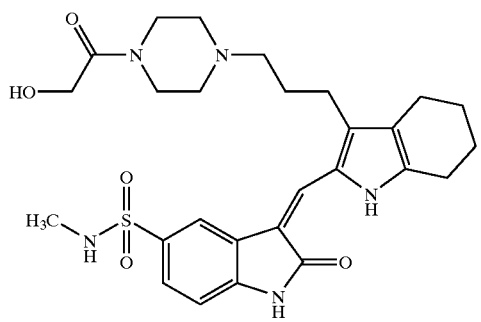

Step 1:

Acetic acid 2-{4-[3-(2-formyl-4,5,6,7-tetrahydro-1H-indol-3-yl)-propyl]-piperazin-1-yl}-2-oxo-ethyl ester was prepared as described in Example 8 but substituting ethyl chloroformate with acetoxyacetyl chloride. Thin layer chromatography (dichloromethane: methanol 20:1) showed two major spot. The reaction mixture was concentrated and purified by flash chromatography, eluting with (dichloromethane/methanol 50/1, 40/1, 30/1, 20/1) to give two fractions of the desired product product.

Step 2:

Each fraction of acetic acid 2-{4-[3-(2-formyl-4,5,6,7-tetrahydro-1H-indol-3-yl)-propyl]-piperazin-1-yl}-2-oxo-ethyl ester was treated separately with potassium carbonate (3.0 eq.) in 6 ml of (methanol/ water 4/1). The two reactions were stirred at room temperature for overnight. Thin layer chromatography (dichloromethane: methanol 15:1) for both reactions showed the same spot and also LCMS showed that they have the same molecular weight. The two reactions were combined and the solvent was evaporated. The formed solid was washed with 30 ml of (dichloromethane/methanol 10/1) three times and sonicated. The liquid was collected and concentrated to give 268 mg of 3-{3-[4-(2-hydroxyacetyl)piperazin-1-yl]-propyl}-4,5,6,7-tetrahydro-1H-indole-2-carbaldehyde.

Step 3:

3-{3-[4-(2-Hydroxy-acetyl)-piperazin-1-yl]-propyl}-4,5,6,7-tetrahydro-1H-indole-2-carbaldehyde (134 mg, 0.3 mmol) was condensed with 5-methylaminosulfonyloxindole (76 Mg, 0.33 mmol) following the procedure used in Example 1 to give 58 mg of the desired product.

Example 14

Synthesis of 5-ethanesulfonyl-3-[1-(3-{3-[4-(2-hydroxyacetyl)-piperazin-1-yl]-propyl}-4,5,6,7-tetrahydro-1H-indol-2-yl)-meth-(Z)-ylidene]-1,3-dihydro-indol-2-one

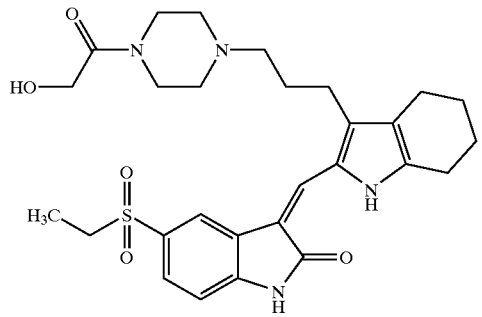

3-{3-[4-(2-Hydroxy-acetyl)-piperazin-1-yl]-propyl}-4,5,6,7-tetrahydro-1H-indole-2-carbaldehyde (134 mg, 0.3 mmol), prepared as described in Example 13, was condensed with 5-ethylsulfonyloxindole (102 mg, 72% pure) following the procedure used in Example 1. Dark solid was precipitated out and purified by flash chromatography, eluting with (dichloromethane/methanol 10/1) to give 46 mg of the desired product.

Example 15

Synthesis of 2-Oxo-3-[1-[3-(3-piperazin-1-yl-propyl)-4,5,6,7-tetrahydro-1H-indol-2-yl]-meth-(Z)-ylidene]-2,3-dihydro-1H-indole-5-sulfonic acid methylamide

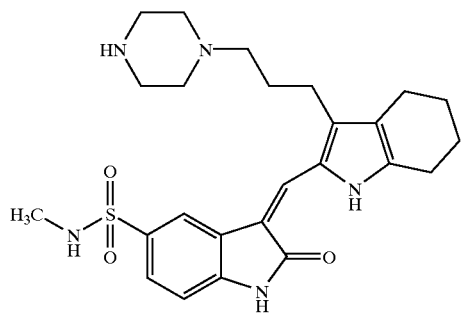

3-(3-Piperazin-1-yl-propyl)-4,5,6,7-tetrahydro-1H-indole-2-carbaldehyde (61 mg, 0.22 mmol), prepared as described in Steps 1–3, Example 8 above, was condensed with 5-methylaminosulfonyloxindole (46 mg, 0.2 mmol) following the procedure used in Example 1 to precipitate 24 mg of the desired product as as a yellow solid.

Example 16

Synthesis of 4-(3-{2-[5-ethanesulfonyl-2-oxo-1,2-dihydro-indol-(3Z)-ylidenemethyl]-4,5,6,7-tetrahydro-1H-indol-3-yl}-propyl)-piperazine-1-carbaldehyde

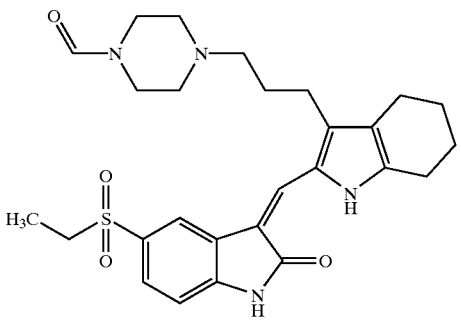

3-[3-(4-Formyl-piperazin-1-yl)-propyl]-4,5,6,7-tetrahydro-1H-indole-2-carbaldehyde (91 mg, 0.3 mmol), prepared as described in Example 8, Steps 1–4 above, was condensed with 5-ethylsulfonyloxindole (67 mg, 0.3 mmol, 50%pure) following the procedure used in Example 1 above. The reaction mixture was purified by flash chromatography using (dichloromethane: methanol 30/1, 20/1, 15/1) to give (100 mg, 64% yield) of the desired product.

Example 17

Synthesis of [4-(3-{2-[5-methylsulfamoyl-2-oxo-1,2-dihydro-indol-(3Z)-ylidenemethyl]-4,5,6,7-tetrahydro-1H-indol-3-yl}-propyl)-piperazin-1-yl]-acetic acid ethyl ester

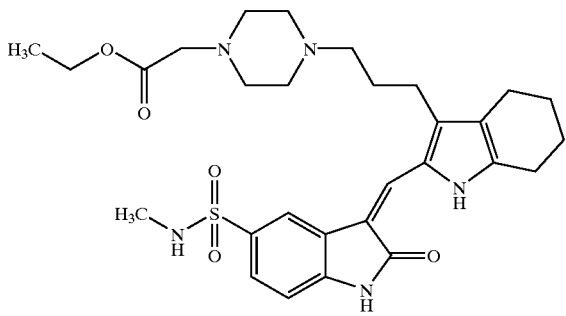

Step 1:
3-(3-Piperazin-1-yl-propyl)-4,5,6,7-tetrahydro-1H-indole-2-carbaldehyde (170 mg, 0.62 mmol), prepared as described in Example 8, was mixed with bromo-acetic acid ethyl ester (89 ml, 0.8 mmol, 1.3 eq.) and potassium carbonate (342 mg, 2.5 mmol, 4 eq.) in dimethylformamide. The mixture was stirred at room temperature overnight. The salt was filtered out and the filterate was rotary evaporated and purified by flash chromatography, eluting with (dichloromethane/methanol 40/1, 30/1) to give 140 mg of {(4-[3-(2-formyl-4,5,6,7-tetrahydro-1H-indol-3-yl)-propyl]-piperazin-1-yl}-acetic acid ethyl ester.
Step 2:
{(4-[3-(2-formyl-4,5,6,7-tetrahydro-1H-indol-3-yl)-propyl]-piperazin-1-yl}-acetic acid ethyl ester (60 mg, 0.1 73 mmol) was condensed with 5-methylaminosulfonyloxindole (45 mg, 0.1 9 mmol, 1.1 eq.) following the procedure used in Example 1 above. The reaction mixture was purified by flash chromatography (dichloromethane/methanol 10/1) to give the desired product.

Example 18

Synthesis of [4-(3-{2-[5-methylsulfamoyl-2-oxo-1,2-dihydro-indol-(3Z)-ylidenemethyl]-4,5,6,7-tetrahydro-1H-indol-3-yl}-propyl)-piperazin-1-yl]-acetic acid

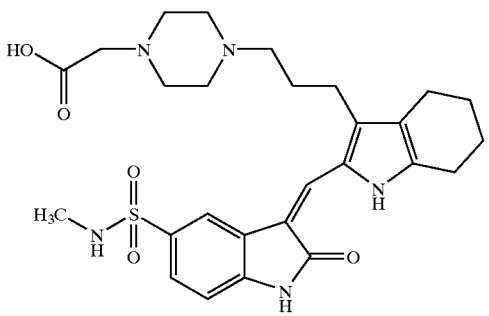

Step 1:
{(4-[3-(2-Formyl-4,5,6,7-tetrahydro-1H-indol-3-yl)-propyl]-piperazin-1-yl}-acetic acid ethyl ester (80 mg), prepared as described in example 17, was treated with potassium carbonate (38 mg, 1 mmol) in methanol/water (6/1) at room temperature for over night. The reaction solution was rotary evaporated and the residue was washed with dichloromethane/methanol (10/1) 3 times. The combined organic solution was concentrated till dryness to give {(4-[3-(2-formyl-4,5,6,7-tetrahydro-1H-indol-3-yl)-propyl]-piperazin-1-yl}-acetic acid.
Step 2:
{(4-[3-(2-Formyl-4,5,6,7-tetrahydro-1H-indol-3-yl)-propyl]-piperazin-1-yl}-acetic acid (50 mg, 0.15 mmol) was condensed with 5-methylaminosulfonyloxindole (40 mg, 0.15 mmol) following the procedure used in Example 1. The formed solid was purified by flash chromatography, eluting with (dichloromethane: methanol 6:1 followed by 4:1:0.01 acetic acid) to give 65 mg of the desired product.

Example 19

Synthesis of [4-(3-{2-[5-ethanesulfonyl-2-oxo-1,2-dihydro-indol-(3Z)-ylidenemethyl]-4,5,6,7-tetrahydro-1H-indol-3-yl}-propyl)-piperazin-1-yl]-acetic acid

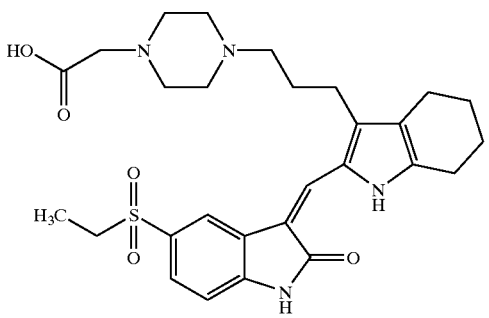

{(4-[3-(2-Formyl-4,5,6,7-tetrahydro-1H-indol-3-yl)-propyl]-piperazin-1-yl}-acetic acid (50 mg, 0.15 mmol), prepared as described in Example 18, was condensed with 5-ethylsulfonyloxindole (66 mg, 60% pure) following the same procedure used in example 1. The formed solid was purified by flash chromatography, eluting with (dichloromethane: methanol 8:1, 5:1:0.01 acetic acid) to give 25 mg of the desired product.

Example 20

Synthesis of 3-[1-{3-[3-(4-hydroxy-piperidin-1-yl)-propyl]-4,5,6,7-tetrahydro-1H-indol-2-yl}-meth-(Z)-ylidene]-2-oxo-2,3-dihydro-1H-indole-5-sulfonic acid methylamide

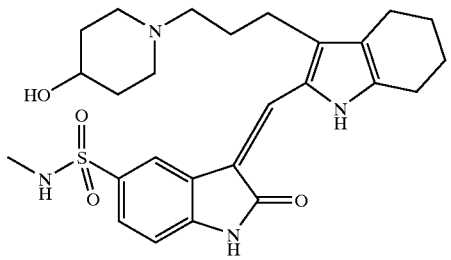

Step 1:

3-[3-(4-Hydroxy-piperidin-1-yl)-3-oxo-propyl]-1,5,6,7-tetrahydro-indol-4-one was prepared by following the procedure described for the synthesis of 4-[3-(4-oxo-4,5,6,7-tetrahydro-1H-indol-3-yl)-propionyl]-piperazine-1-carboxylic acid tert-butyl ester (Step 1 of example 8) by substituting tert-butyl 1-piperazinecarboxylate with piperidin-4-ol.

Step 2:

1-[3-(4,5,6,7-Tetrahydro-1H-indol-3-yl)propyl]-piperidin-4-ol was prepared following the procedure used for the synthesis of 3-(3-piperazin-1-yl-propyl)-4,5,6,7-tetrahydro-1H-indole (see Step 3 of Example 8).

Step 3:

3-[3-(4-Hydroxy-piperidin-1-yl)- propyl]-4,5,6,7-tetrahydro-1H-indole-2-carbaldehyde was prepared utilizing the procedure described for 3-(3-piperazin-1-yl-propyl)-4,5,6,7-tetrahydro-1H-indole-2-carbaldehyde (Example 8, Step 4).

Step 4:

3-[3-(4-Hydroxy-piperidin-1-yl)-propyl]-4,5,6,7-tetrahydro-1H-indole-2-carbaldehyde (58 mg, 0.2 mmol) was condensed with 5-methylaminosulfonyloxindole (45 mg, 0.2 mmol) following the procedure used in Example 1 to provide (66 mg, 67%yield) of the desired compound.

Example 21

Synthesis of 5-Ethanesulfonyl-3-[1-{3-[3-(4-hydroxy-piperidin-1-yl)-propyl]-4,5,6,7-tetrahydro-1H-indol-2-yl}-meth-(Z)-ylidene]-1,3-dihydro-indol-2-one

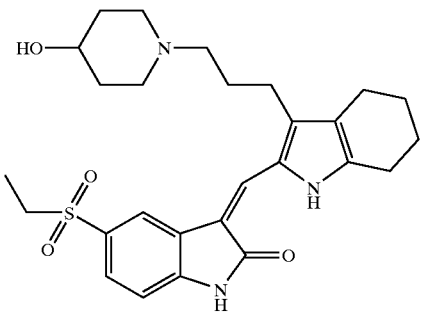

3-[3-(4-Hydroxy-piperidin-1-yl)-propyl]-4,5,6,7-tetrahydro-1H-indole-2-carbaldehyde (58 mg, 0.2 mmol), prepared as described in Example 20, was condensed with 5-ethylsulfonyloxindole (69 mg, 0.2 mmol, 65%pure) following the procedure used in Example 1 to provide 31 mg of the desired compound.

Example 22

Synthesis of 3-[1-(3-{3-[4-(2-hydroxy-ethyl)-piperazin-1-yl]-propyl}-4,5,6,7-tetrahydro-1H-indol-2-yl)-meth-(Z)-ylidene]-2-oxo-2,3-dihydro-1H-indole-5-sulfonic acid methylamide

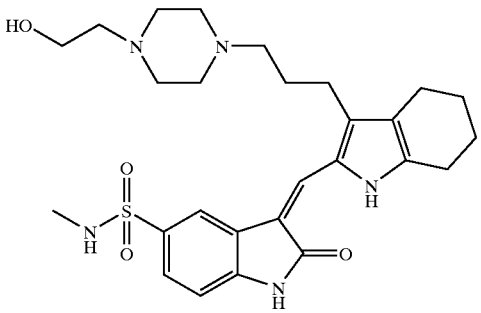

3-{3-[4-(2-Hydroxyethyl)-piperazin-1-yl]-propyl}-4,5,6,7-tetrahydro-1H-indole-2-carbaldehyde (64 mg, 0.2 mmol), prepared by following the procedure described for 3-[3-(4-hydroxy-piperidin-1-yl)-propyl]-4,5,6,7-tetrahydro-1H-indole-2-carbaldehyde (Example 20), was condensed with 5-methylaminosulfonyloxindole (46 mg, 0.2 mmol) to give 66 mg of the desired product.

Example 23

Synthesis of 5-ethanesulfonyl-3-[1-(3-{3-[4-(2-hydroxy-ethyl)-piperazin-1-yl]-propyl}-4,5,6,7-tetrahydro-1H-indol-2-yl)-meth-(Z)-ylidene]-1,3-dihydro-indol-2-one

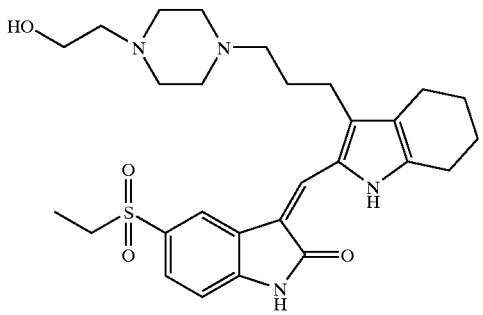

3-{3-[4-(2-Hydroxy-ethyl)-piperazin-1-yl]- propyl}-4,5,6,7-tetrahydro-1H-indole-2-carbaldehyde (64 mg, 0.2 mmol), prepared by following the procedure described for 3-[3-(4-hydroxy-piperidin-1-yl)- propyl]-4,5,6,7-tetrahydro-1H-indole-2-carbaldehyde (example 20), was condensed with 5-ethylsulfonyloxindole (Example 5) (69 mg, 0.2 mmol, 65%pure). The reaction solution was purified by flash chromatography, eluting with dichloromethane/methanol (20/1, 15/1 then 10/1) to provide 63 mg of the desired compound.

Example 24

Synthesis of 3-[1-{3-[3-(3,5-dimethyl-piperazin-1-yl)-propyl]-4,5,6,7-tetrahydro-1H-indol-2-yl}-meth-(Z)-ylidene]-2-oxo-2,3-dihydro-1H-indole-5-sulfonic acid methylamide

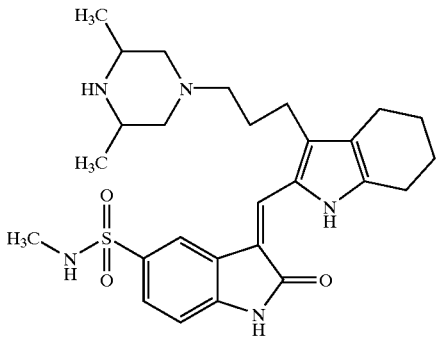

Step 1:

3-[3-(3,5-Dimethyl-piperazin-1-yl)-propyl]-4,5,6,7-tetrahydro-1H-indole-2-carbaldehyde was prepared following the procedure described for 3-(3-methylamino-propyl)-4,5,6,7-tetrahydro-1H-indole-2-carbaldehyde (Example 1) by substituting dimethylamine with 2,6-dimethylpiperazine.

Step 2:

3-[3-(3,5-Dimethyl-piperazin-1-yl)-propyl]-4,5,6,7-tetrahydro-1H-indole-2-carbaldehyde (67 mg, 0.22 mmol) was condensed with 5-methylaminosulfonyloxindole (50 mg, 0.22 mmol) following the procedure used in Example 1 to provide (68 mg, 60% yield) of the desired compound.

Example 25

Synthesis of 3-[1-{3-[3-(3,5-dimethyl-piperazin-1-yl)-propyl]-4,5,6,7-tetrahydro-1H-indol-2-yl}-meth-(Z)-ylidene]-5-ethanesulfonyl-1,3-dihydro-indol-2-one

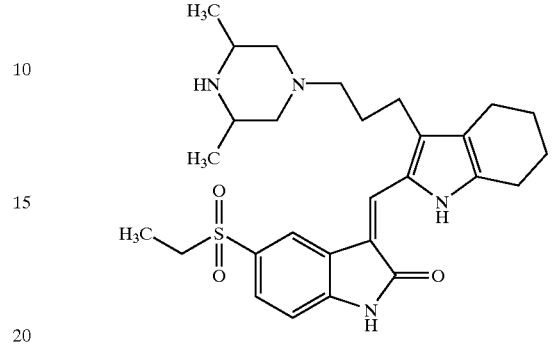

3-[3-(3,5-Dimethyl-piperazin-1-yl)-propyl]-4,5,6,7-tetrahydro-1H-indole-2-carbaldehyde (62 mg, 0.22 mmol), prepared as described in Example 24, was condensed with 50 mg (0.22 mmol) of 5-ethylsulfonyloxindole to provide (60 mg, 53% yield) of the desired compound.

Example 26

Synthesis of 3-[1-[3-(3-Morpholin-4-yl-propyl)-4,5,6,7-tetrahydro-1H-indol-2-yl]-meth-(Z)-ylidene]-2-oxo-2,3-dihydro-1H-indole-5-sulfonic acid (2-hydroxy-ethyl)-amide

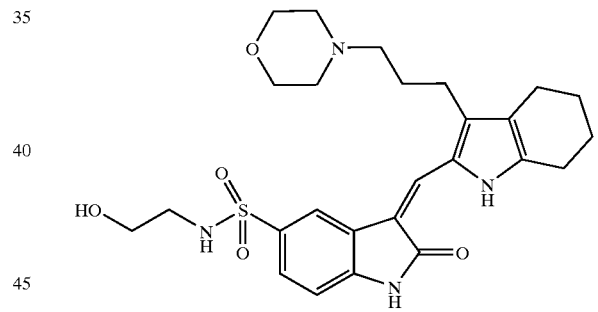

Step 1:

3-(3-Morpholin-4-yl-propyl)-4,5,6,7-tetrahydro-1H-indole-2-carbaldehyde was prepared utilizing the procedure described for 3-(3-dimethylamino-propyl)-4,5,6,7-tetrahydro-1H-indole-2-carbaldehyde (Example 1) but substituting dimethylamine with morpholine.

Step 2:

Ethanolamine (1.5 ml, 25 mmol) was added to 5-chlorosulfonyloxindole (2.3 g, 10 mmol) in 60 ml of dimethylformamide. The reaction mixture was stirred at room temperature for 4 hours. Thin layer chromatography (dichloromethane/methanol 8/1) showed no starting material. The reaction solution was rotary evaporated at low temperature (30° C.) and the residue was purified by flash chromatography, eluting with dichloromethane/methanol (10/1) to provide 2.7 g of 5-sulfonic acid (2-hydroxy-ethyl) amide oxindole.

Step 3:

3-(3-Morpholin-4-yl-propyl)-4,5,6,7-tetrahydro-1H-indole-2-carbaldehyde (55.2 mg, 0.2 mmol) was condensed with 5-sulfonic acid (2-hydroxy-ethyl) amide oxindole (51.2 mg, 0.2 mmol) to provide (57.5 mg, 56% yield) of the desired compound.

Example 27

Synthesis of 3-[1-[3-(3-Dimethylamino-propyl)-4,5,6,7-tetrahydro-1H-indol-2-yl]-meth-(Z)-ylidene]-2-oxo-2,3-dihydro-1H-indole-5-sulfonic acid (2-hydroxy-ethyl)-amide

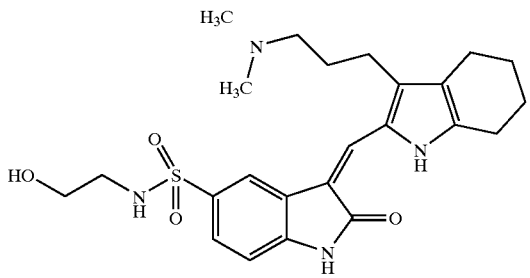

3-(3-Dimethylamino-propyl)-4,5,6,7-tetrahydro-1H-indole-2-carbaldehyde (47 mg, 0.2 mmol), prepared as described in Example 1, was condensed with 5-sulfonic acid (2-hydroxy-ethyl) amide oxindole (51 mg, 0.2 mmol) to provide (43.3 mg, 46% yield) of the desired compound.

Example 28

Synthesis of 3-[1-(3-{3-[(2-hydroxy-ethyl)-methyl-amino]-propyl}-4,5,6,7-tetrahydro-1H-indol-2-yl)-meth-(Z)-ylidene]-2-oxo-2,3-dihydro-1H-indole-5-sulfonic acid methylamide

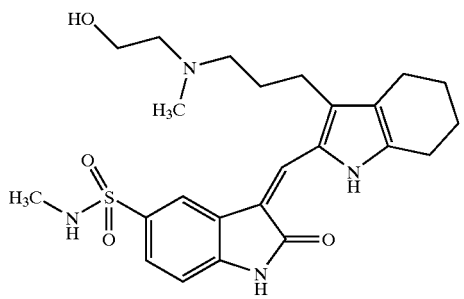

Step 1:
Potassium carbonate (552 mg) and 156 µl (2 mmol) of 2-iodoethanol were added to methyl-[3-(4,5,6,7-tertrahydro-1H-indol-3-yl)-propyl]amine (192 mg, 1 mmol) in 4 ml of acetonitrile. The mixture was stirred at room temperature for 24 hours. The reaction solution was rotary evaporated and purified by flash chromatography, eluting with dichloromethane/methanol 10/1 to provide 200 mg of 2-{methyl-[3-(4,5,6,7-tertrahydro-1H-indol-3-yl)-propyl]-amino}-ethanol.
Step 2:
3-{3-[(2-Hydroxyethyl)-methyl-amino)]-propyl}-4,5,6,7-tetrahydro-1H-indole-2-carbaldehyde was prepared utilizing the procedure described for 3-(3-dimethylamino-propyl)-4,5,6,7-tetrahydro-1H-indole-2-carbaldehyde, Step 4 of Example 1, starting with 2-{methyl-[3-(4,5,6,7-tertrahydro-1H-indol-3-yl)-propyl]-amino}ethanol.
Step 3:
3-{3-[(2-Hydroxy-ethyl)-methylamino)]-propyl}-4,5,6,7-tetrahydro-1H-indole-2-carbaldehyde (53 mg, 0.2 mmol) was condensed with 5-methylamino-sulfonyloxindole (46 mg, 0.2 mmol) following the procedure used in Example 1. The reaction mixture was purified by flash chromatography, eluting with dichloromethane/methanol (20/1, 15/1, 10/1) to provide (53 mg, 56% yield) of the desired compound.

Example 29

Synthesis of 5-Ethanesulfonyl-3-[1-(3-{3-[(2-hydroxy-ethyl)-methyl-amino]-propyl}-4,5,6,7-tetrahydro-1H-indol-2-yl)-meth-(Z)-ylidene]-1,3-dihydro-indol-2-one

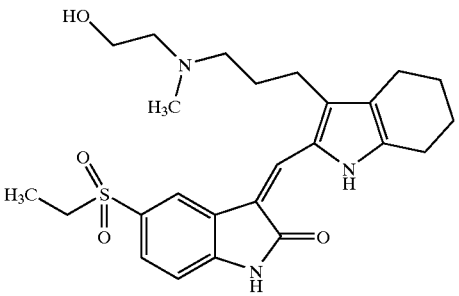

3-{3-[(2-Hydroxyethyl)-methyl-amino)]-propyl}-4,5,6,7-tetrahydro-1H-indole-2-carbaldehyde (53 mg, 0.2 mmol), prepared as described in Example 28, was condensed with 5-ethylsulfonyloxindole (45 mg, 0.2 mmol) of following the same procedure used in example 1. The reaction mixture was purified by flash chromatography, eluting with dichloromethane/methanol (30/1, 20/1, 15/1) to provide (58 mg, 56% yield) of the desired compound.

Biological Examples

Example 1

Src Family Kinase Biochemical Assays—In Vitro Assay

The Src family kinase biochemical assays make use of purified recombinant kinases, synthetic peptide substrates and purified ATP to measure the ability of compounds to inhibit the protein tyrosine kinase activity of Src, Fyn Lyn Yes and Lck) which are members of the Src family of protein tyrosine kinases. The detection of protein tyrosine phosphorylation is achieved using an anti-phosphotyrosine time resolved fluorescence resonance energy transfer (TRFRET) method ((see., He Y. Assay development for high-throughput screening: Practical considerations in drug discovery, In W. Hori and L. M Savage (eds.): High-Throughput Screening. Novel Assay Design, Rapid Target Development and Accelerated Level Optimization. IBC Library Series, Southborough, Mass., pp. 115–128 (1997); Hemmilä I., and Webb S., Time-resolved fluorometry: an overview of the labels and core technologies for drug screening applications. *Drug Discovery Today* 2: 373–81 (1997); and Hemmilä I. LANCE™, Homogeneous assay platform for HTS. *J. Biomol. Screen* 4: 303–7 (1999)).

Recombinant glutathione-S-transferase (GST)/Src family kinase fusion proteins (recombinant kinase) are generated using standard molecular biology, protein expression and purification procedures (see Molecular Cloning: A Laboratory Manual by T. Maniatis et al., ASIN: 0879693096; Short Protocols in Molecular Biology, 4$^{th}$ Ed., by F. M. Ausubel et al., John Wiley and Sons; ISBN: 047132938X; Cloning, Gene Expression and Protein Purification: Experimental Procedures and Process Rationale by Charles C. Hardin; Molecular Cloning: A Laboratory Manual by Joseph Sambrook et al., and Basic Methods in Molecular Biology by Leonard G. et al.). Compounds that are being evaluated are incubated with recombinant kinase diluted in a solution buffered with 4-(2-hydroxyethyl)-1-piperazineethanesulfonic acid (HEPES) containing magnesium chloride, manganese chloride, a biotinylated substrate peptide and adenosine triphosphate. The antiphosphotyrosine TRFRET detection is carried out according to standard procedures ((see., He Y. Assay development for high-throughput screening: Practical considerations in drug discovery, In W. Hori and L. M Savage (eds.): High-Throughput Screening. Novel Assay Design, Rapid Target Development and Accelerated Level Optimization. IBC Library Series, Southborough, Mass., pp. 115–128 (1997); Hemmilä I., and Webb S., Time-resolved fluorometry: an overview of the labels and core technologies for drug screening applications. *Drug Discovery Today* 2: 373–81 (1997); and Hemmilä I. LANCE™, Homogeneous assay platform for HTS. *J. Biomol. Screen* 4: 303–7 (1999)).

Example 2

Cellular Assays that Determine the Ability of Compounds to Inhibit Src

Protein Kinase Activity Within Living Cells—In Vitro Assay

Src Actin Ring Assay

The Src Actin Ring assay uses automated fluorescence imaging to quantitate podosome rosettes (actin cytoskeletal structures) that are formed in cells due to the catalytic activity of Src ((see., Blake R. A, et al., "SU6656, a selective Src family kinase inhibitor, used to probe growth factor signaling". *Molecular and Cellular Biology*, December 2000, p 9018–9027; and Blake R. A. "Cellular screening assays using fluorescence microscopy. Current Opinion in Pharmacology 2001, 1. (In Press)).

Standard molecular biology, tissue culture and cell transfection techniques are used to generate stable clones of NIH3T3 cells that express the mutant form of the human Src gene with tyrosine 530 mutated to a phenylalanine. These cells will be referred to as NIH3T3Y530F. The NIH3T3 cells from which the NIH3T3Y530F cells were derived will be referred to as parental NIH3T3 cells. NIH3T3Y530F cells are seeded in a multi-well plate leaving several control wells left empty. Parental NIH3T3 cells are seeded in the remaining empty wells. Test compounds are diluted in tissue culture medium and transferred to individual wells of the multi-well plate containing NIH3T3Y530F cells. The cells are incubated in the presence of compound for periods ranging between 1 to 24 hours, then fixed using paraformaldehyde (according to standard immunofluorescence procedures). The actin and DNA is stained using fluorescent-labeled phalloidin and bisbenzimide respectively. The podosome rosettes within the cells are quantitated using a Cellomics (Pittsburgh) ArrayScan II using standard imaging software available on the ArrayScan II and measured relative to the number of nuclei. The podosome rosettes in compound treated NIH3T3Y530F are compared relative to those in untreated NIH3T3Y530F and the parental NIH3T3 cells to obtain percentage inhibition values, dose response curves and IC$_{50}$ values.

Src Cellular Protein Kinase Assay

The Src cellular protein kinase assay (SrcpTyr assay) measures the total protein phosphotyrosine level in cells expressing an activated mutant of Src. NIH3T3Y530F cells are generated as described in the Src Actin Ring assay procedure above. NIH3T3Y530F cells and the parental NIH3T3 cells are seeded in a multi-well plate. Test compounds are diluted in tissue culture medium and transferred to individual wells of the multi-well plate containing NIH3T3Y530F cells. The cells are incubated in the presence of compound for periods ranging between 1 to 24 hours, then fixed using paraformaldehyde and permeabilized using detergents such as TritonX100. The total protein phosphotyrosine level is measured using an ELISA procedure as follows. Horseradish peroxidase (HRP) linked anti-phosphotyrosine is added to each well containing fixed and permeabilized cells and incubated for 1 to 2 hours. Unbound antibody is washed off and the HRP substrate 2,2'-Azino-bis-(3-ethylbenzthiazoline-6-sulfonic acid (ABTS) is added. Standard spectroscopic techniques are used to quantitate the concentration of ABTS product.

Src Dependent Cellular Motility Assay

The Src dependent cellular motility assay measures the motility of cells expressing an activated mutant of Src relative to that of the parental cells. This assay makes use of reagents and protocols supplied by Cellomics, Pittsburgh. NIH3T3Y530F cells are generated as described in the Src Actin Ring assay procedure above. Multiwell tissue culture plates are coated with poly-L-lysine and fluorescent microbeads (Cellomics, Pittsburgh). NIH3T3Y530F and parental NIH3T3 cells are seeded into the multiwell plate. The cells are incubated in the presence of compound for 24 hours and fixed using paraformaldehyde. The motility of the cells is measured using automated fluorescence imaging by an ArrayScanII (Cellomics, Pittsburgh) according to the manufacturer's instructions.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula (I):

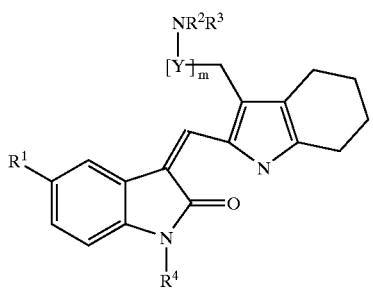

wherein:
Y is a methylene or ethylene;
m is 0 or 1;
$R^1$ is $SO_2NR^6R^7$ where $R^6$ is hydrogen and $R^7$ alkyl;
$R^2$ and $R^3$ together with the nitrogen atom to which they are attached form a heterocycloamino group, wherein said heterocycloamino group is a piperazine-1-yl moiety;
$R^4$ is hydrogen; or
a pharmaceutically acceptable salt thereof.

2. The compound of claim 1 wherein m is 1 and Y is ethylene.

3. The compound of claim 1 wherein said piperazin-1-yl moiety is optionally substituted with one, or two substituents independently selected from alkyl, alkoxycarbonyl, acyl, hydroxyalkylcarbonyl, alkoxycarbonylalkyl, carboxyalkyl, hydroxy, or hydroxyalkyl.

4. A pharmaceutical composition, comprising a compound or salt of claims 1 and a pharmaceutically acceptable carrier or excipient.

* * * * *